(12) United States Patent
Wang et al.

(10) Patent No.: US 12,303,161 B2
(45) Date of Patent: May 20, 2025

(54) THROMBUS TREATMENT PLATFORM

(71) Applicant: SUZHOU VENMED TECHNOLOGY CO., LTD., Suzhou (CN)

(72) Inventors: Xiaotian Wang, Suzhou (CN); Lei Zhang, Suzhou (CN); Haiquan Feng, Suzhou (CN); Xiaoqiang Li, Suzhou (CN); Yonggang Wang, Suzhou (CN); Lijuan Guan, Suzhou (CN); Jing Li, Suzhou (CN)

(73) Assignee: SUZHOU VENMED TECHNOLOGY CO., LTD, Suzhou (CN)

( * ) Notice: Subject to any disclaimer, the term of this patent is extended or adjusted under 35 U.S.C. 154(b) by 616 days.

(21) Appl. No.: 17/628,936

(22) PCT Filed: Dec. 25, 2020

(86) PCT No.: PCT/CN2020/139595
§ 371 (c)(1),
(2) Date: Jan. 21, 2022

(87) PCT Pub. No.: WO2021/248878
PCT Pub. Date: Dec. 16, 2021

(65) Prior Publication Data
US 2022/0249121 A1    Aug. 11, 2022

(30) Foreign Application Priority Data

Jun. 12, 2020  (CN) .......................... 202010534497.0

(51) Int. Cl.
*A61B 17/3207* (2006.01)
*A61B 17/22* (2006.01)
(52) U.S. Cl.
CPC ................ *A61B 17/320758* (2013.01); *A61B 17/320725* (2013.01); *A61B 2017/22074* (2013.01);
(Continued)

(58) Field of Classification Search
CPC .... A61B 17/320758; A61B 17/320725; A61B 2017/22074; A61B 2017/22078; A61B 2017/22079
See application file for complete search history.

(56) References Cited

U.S. PATENT DOCUMENTS

| 10,143,489 | B2 | 12/2018 | Kobayashi et al. |
| 2002/0010487 | A1* | 1/2002 | Evans ............ A61B 17/320758 |
| | | | 606/159 |
| 2010/0030186 | A1* | 2/2010 | Stivland ................ A61M 25/09 |
| | | | 604/528 |

FOREIGN PATENT DOCUMENTS

| CN | 102743207 A | 10/2012 |
| CN | 107348990 A | 11/2017 |

(Continued)

*Primary Examiner* — Brooke Labranche
(74) *Attorney, Agent, or Firm* — AGMON LAW PTE LTD

(57) ABSTRACT

A thrombus treatment platform comprises an aspiration catheter, an aspiration pump, a stirring device and a filter assembly, the filter assembly comprises a filter rod and a filter screen; the stirring device comprises a first catheter, a second catheter, a stirrer and an operating device capable of causing the first catheter and the second catheter to slide relatively so that the stirrer can be switched between the expanded state and the collapsed state; the thrombus treatment platform further comprises a driving device capable of driving the rotation of the stirrer. The present disclosure can remove thrombus under the condition of ensuring relative safety, and is particularly suitable for removing a large number of thrombus in the inferior vena cava, protects venous valves and venous vessel walls, has controllable blood loss and simple operation steps, shortens operation time, and reduces patient hospitalization expenses.

19 Claims, 15 Drawing Sheets

(52) U.S. Cl.
CPC ............... *A61B 2017/22078* (2013.01); *A61B 2017/22079* (2013.01)

(56) References Cited

FOREIGN PATENT DOCUMENTS

| | | |
|---|---|---|
| CN | 207855775 U | 9/2018 |
| CN | 109640847 A | 4/2019 |
| CN | 110312481 A | 10/2019 |
| CN | 210749398 U | 6/2020 |
| CN | 111544081 A | 8/2020 |
| CN | 211300191 U | 8/2020 |
| CN | 212490055 U | 2/2021 |
| EP | 0719111 B1 | 1/2001 |

\* cited by examiner

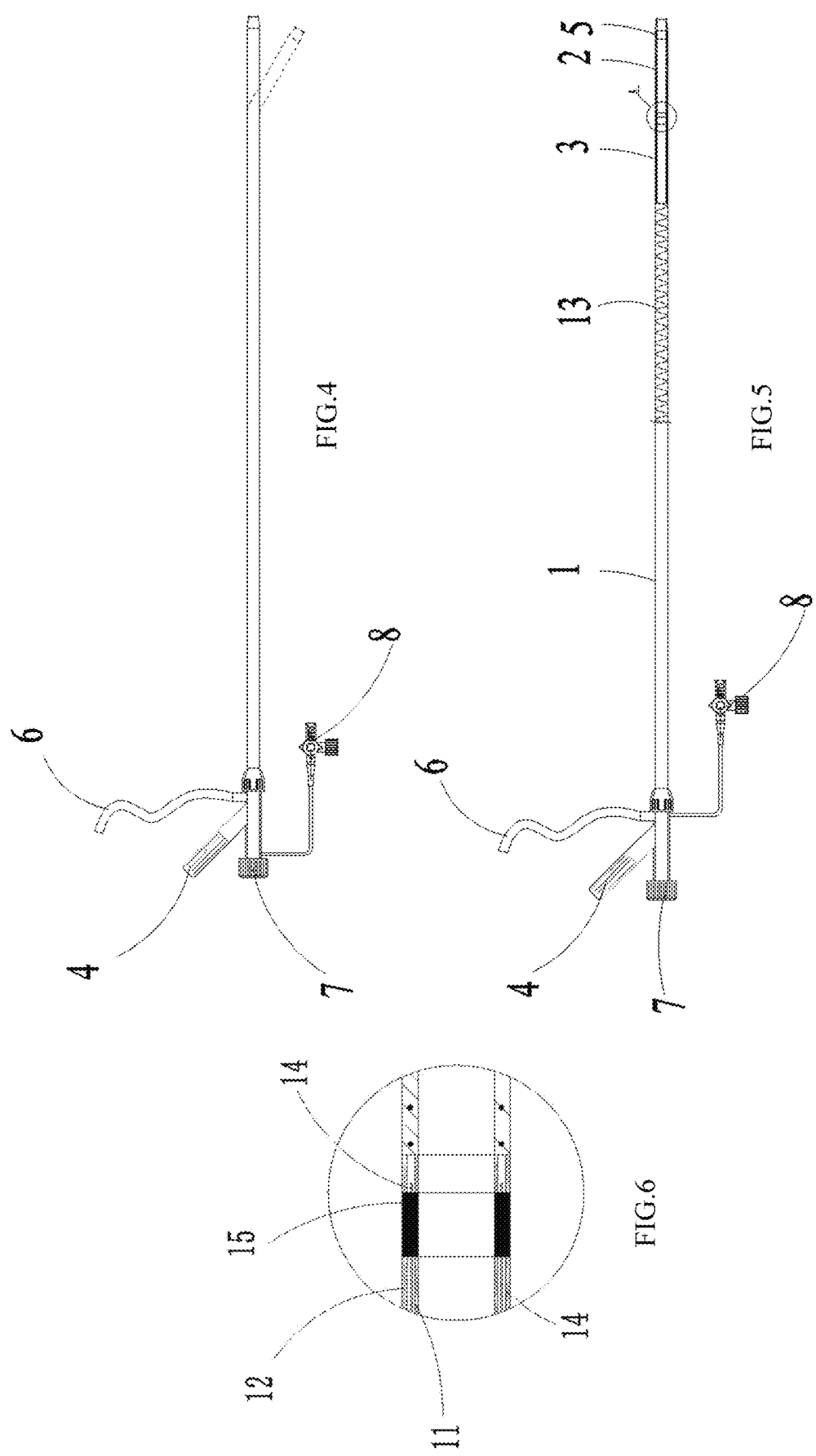

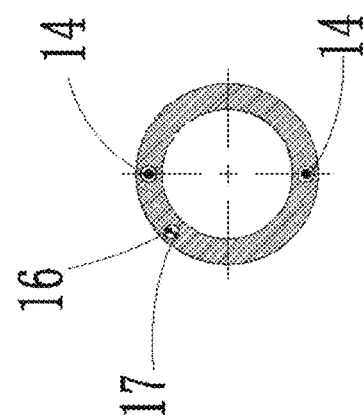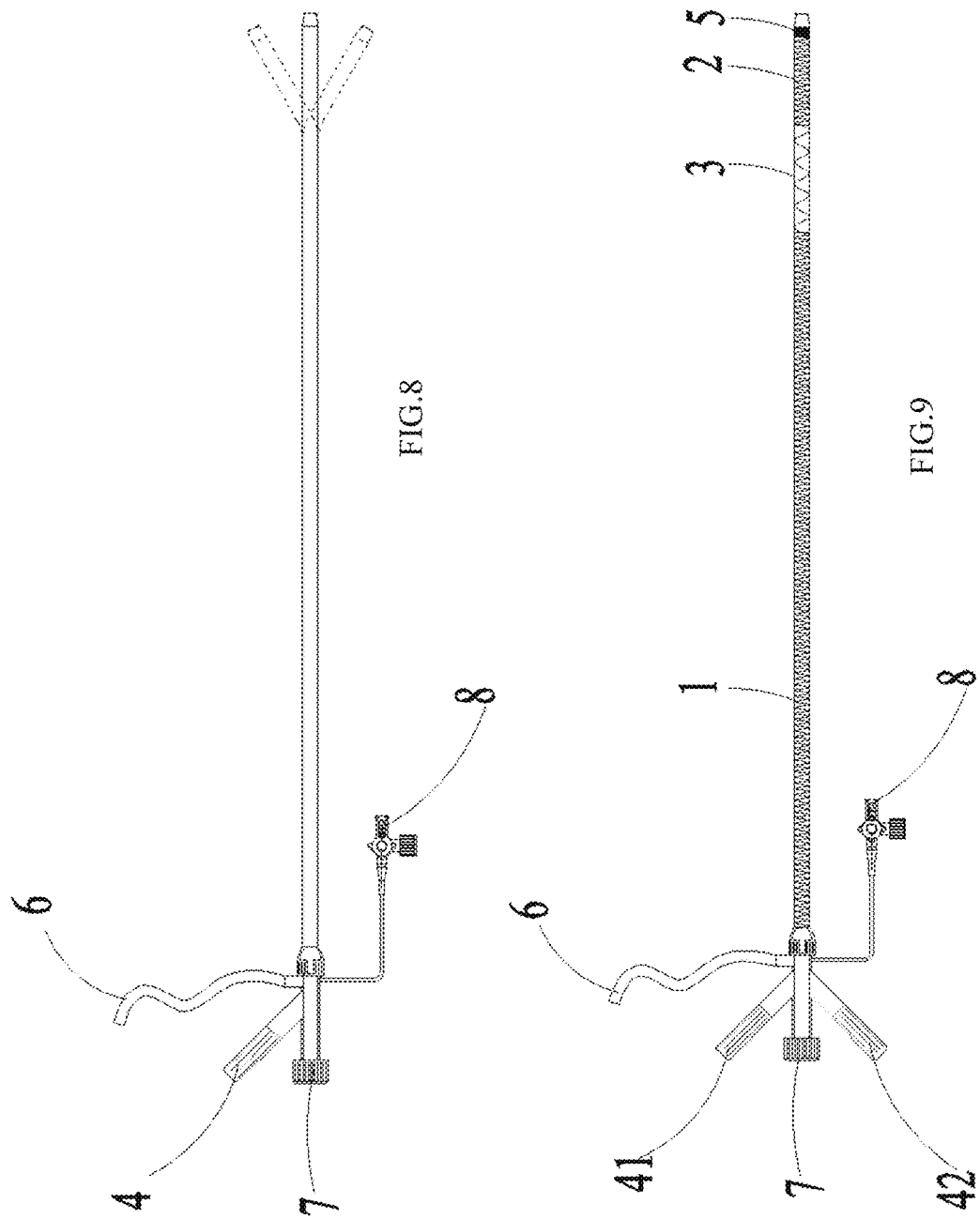

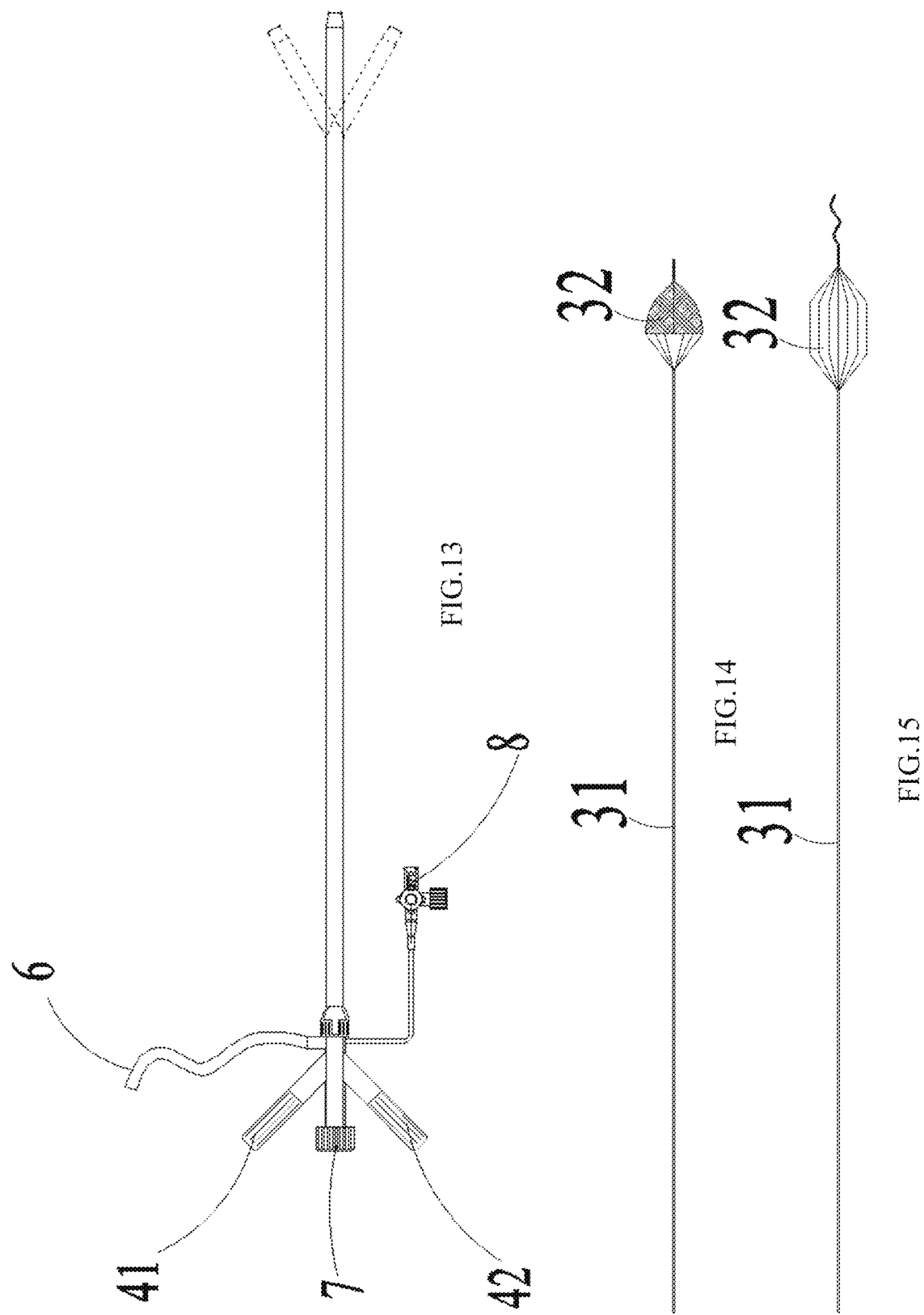

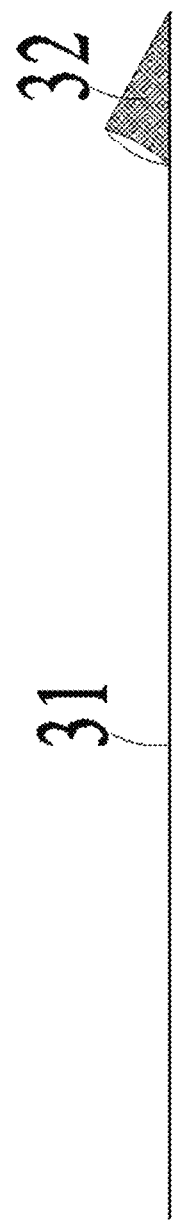
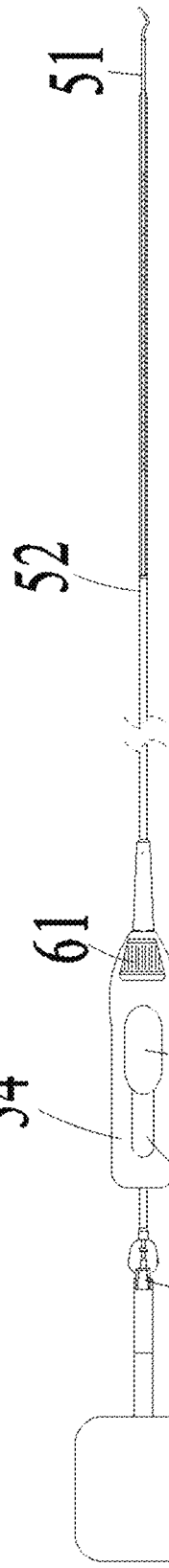
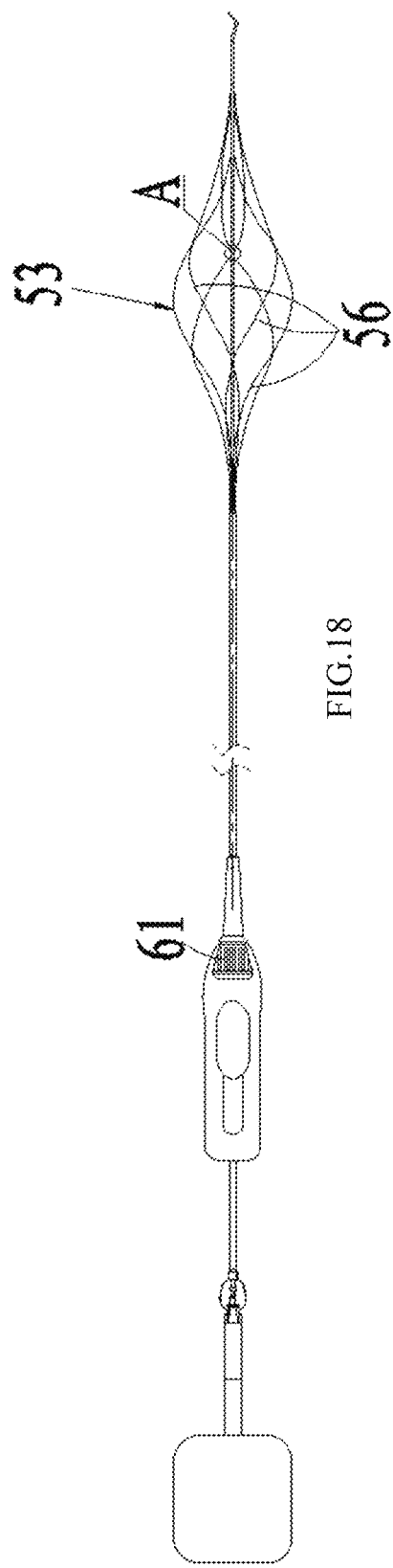
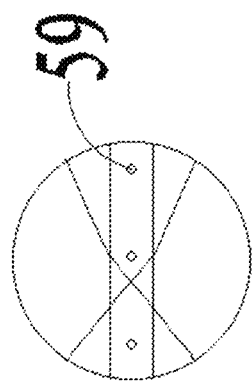
FIG.16
FIG.17
FIG.18
FIG.19

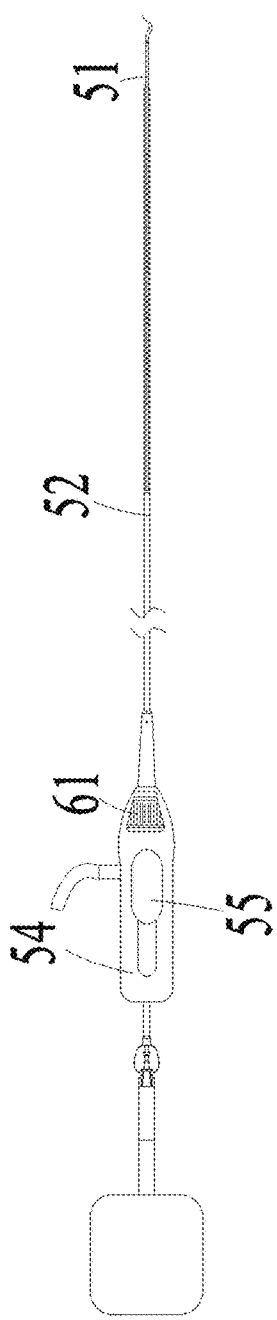
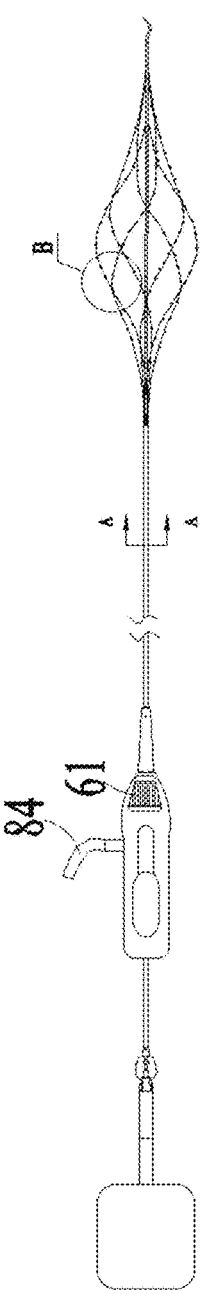
FIG.20
FIG.21
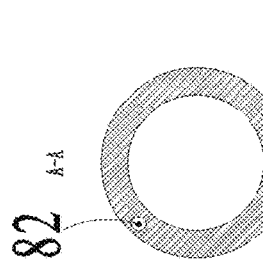
FIG.22
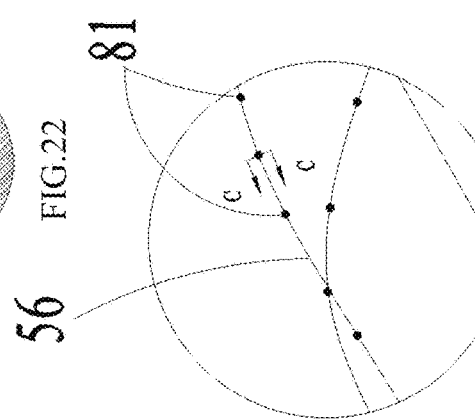
FIG.23
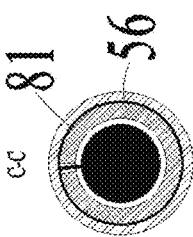
FIG.24

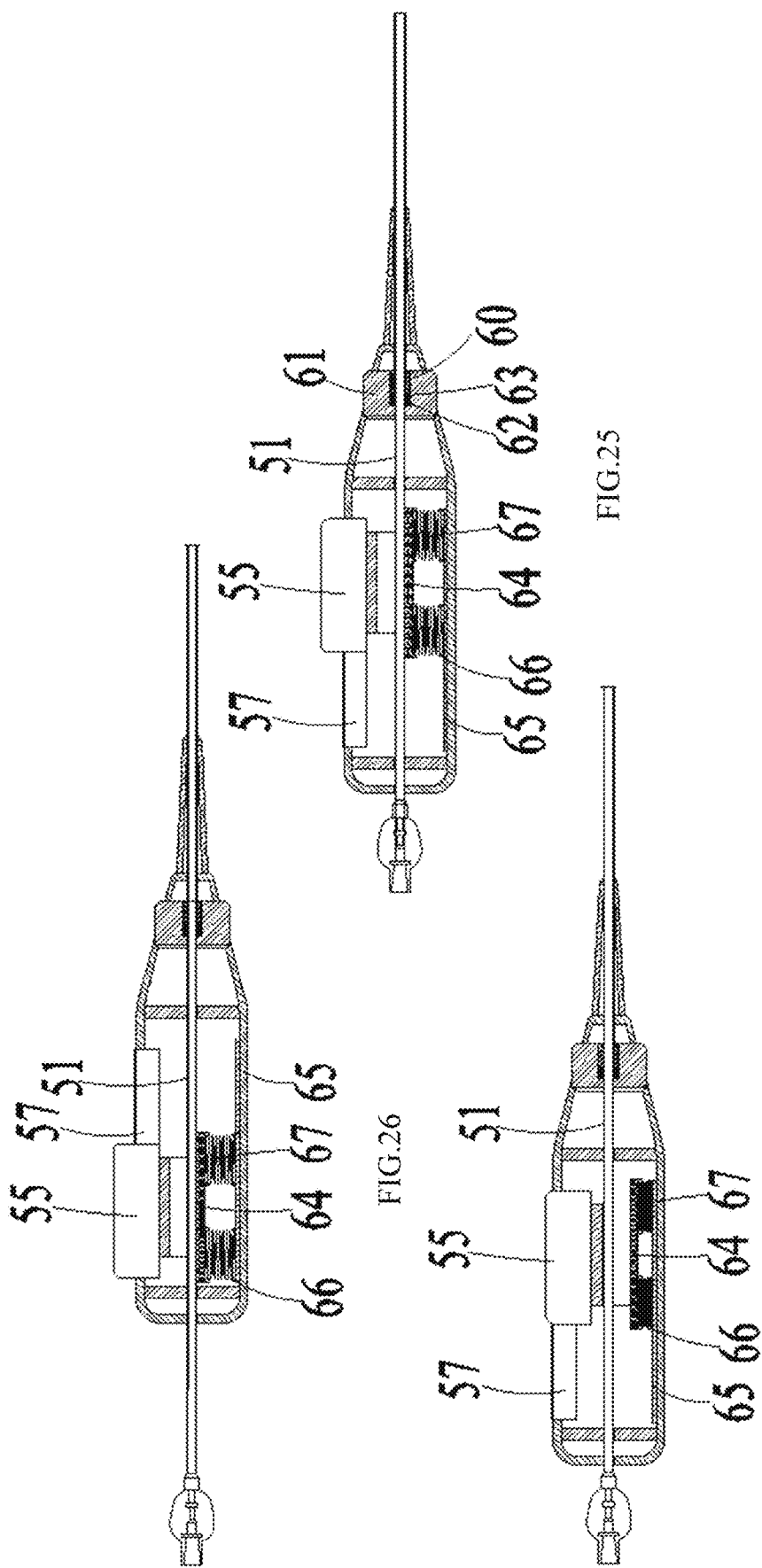

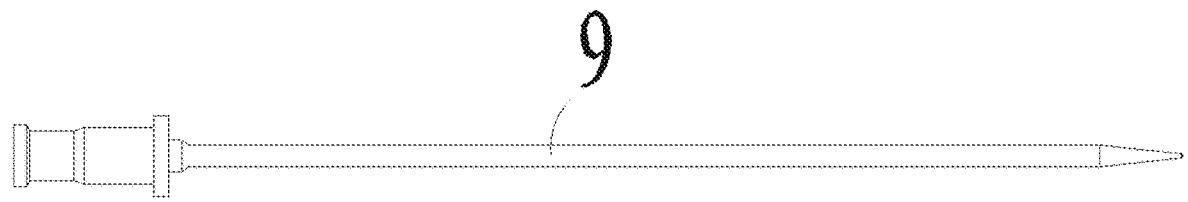
FIG.32
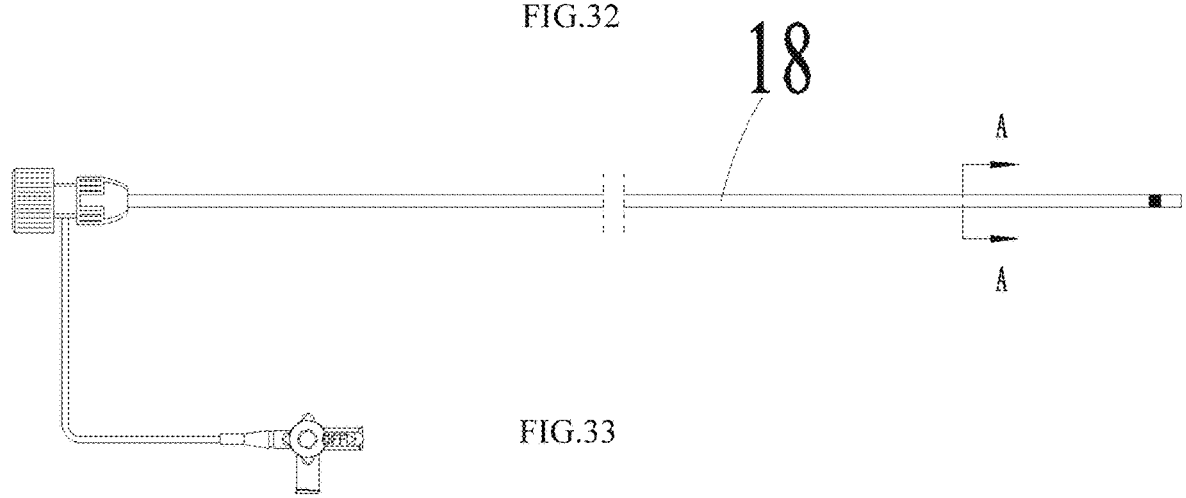
FIG.33
FIG.34
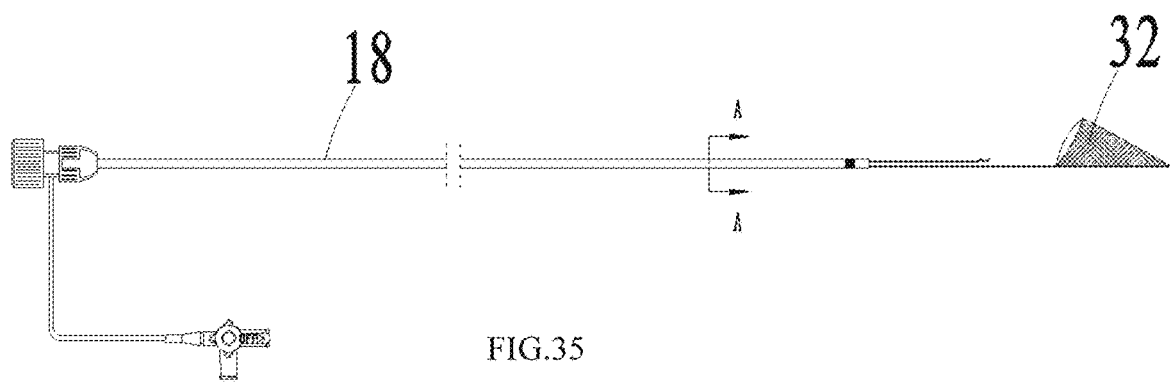
FIG.35

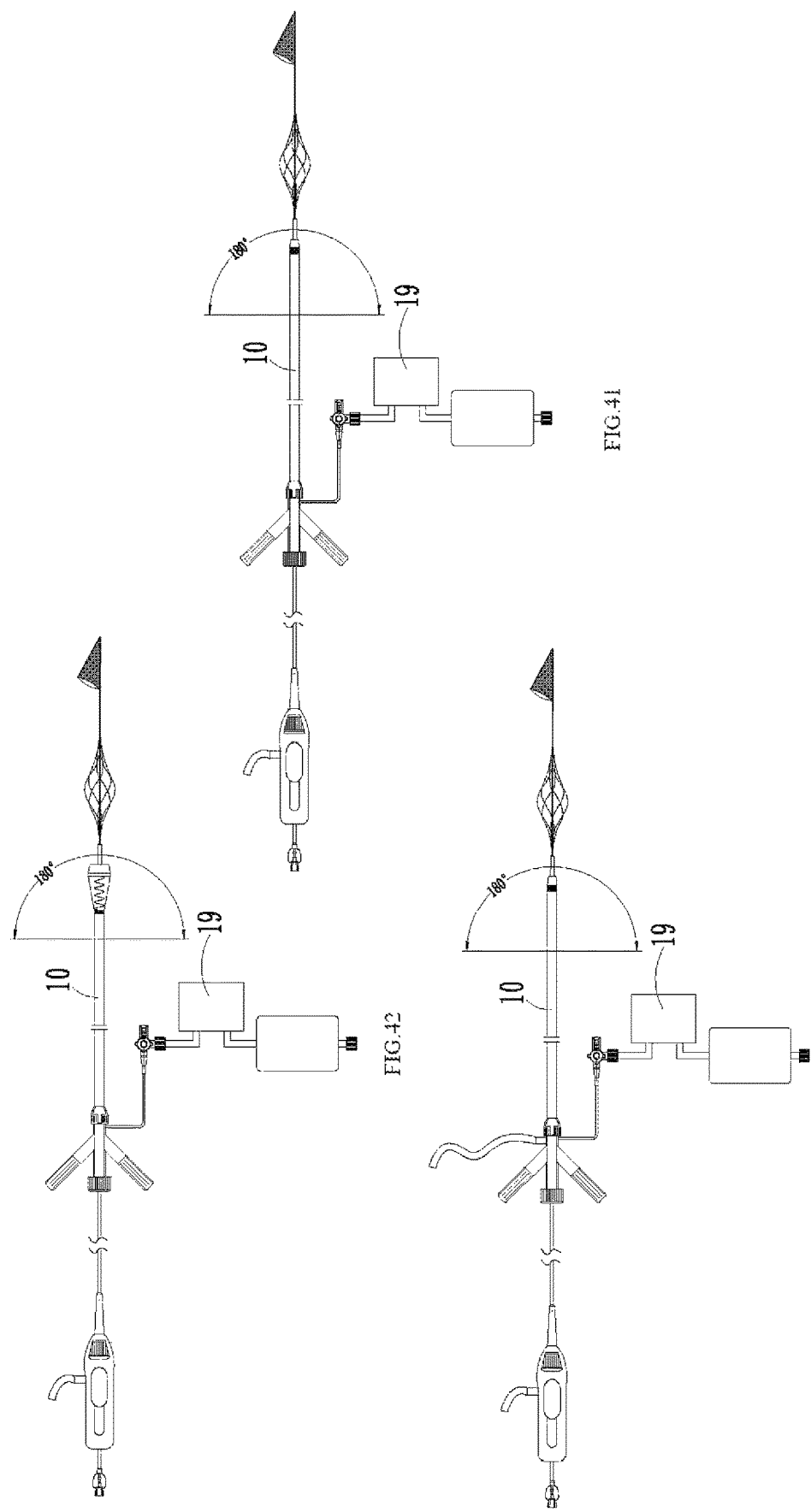

THROMBUS TREATMENT PLATFORM

TECHNICAL FIELD OF THE INVENTION

The present disclosure belongs to the field of medical apparatus and instruments, specifically relates to a thrombus treatment platform.

BACKGROUND OF THE INVENTION

Thrombotic diseases include arterial thrombosis, venous thrombosis, and thromboembolism. The existing treatment methods mainly include vascular incision and thrombectomy, catheter-directed thrombolysis, and percutaneous mechanical thrombectomy. Incision and thrombectomy requires anatomical separation and incision of blood vessels, such as femoral artery incision, femoral vein incision or brachial artery incision, etc.. With the development of endovascular interventional technology and material innovation, this open surgical method is gradually replaced by minimally invasive interventional endovascular therapy, that is, catheter-directed thrombolysis and percutaneous mechanical thrombectomy. Catheter-directed thrombolysis has a high risk of bleeding due to thrombolytic drugs, and its surgical indications are extremely strict. Many patients have contraindications to catheter-directed thrombolysis, so many patients cannot benefit from it.

Based on existing medical knowledge, deep vein thrombosis tends to be large in volume and the thrombus in the acute phase is soft and fragile arterial thrombosis tends to be small in volume, and the thrombus in the acute phase is soft in texture old thrombosis often adheres to the blood vessel wall. As for the old thrombus, the old thrombus is mainly shed by mechanical scraping the blood vessel wall or thrombolytic drugs.

For example, a thrombectomy catheter system that uses a spiral cutter at the front of the catheter to cut the thrombus in a spinning manner and draw the clot out of the body by aspiration, such as the X-sizer thrombectomy catheter system. Chinese patent CN204092102U discloses a new type of peripheral vascular disease thrombus aspiration connector, including: a tube body, a rotating rod, a spiral rotating piece, an arc joint, and a connecting tail base, the tube body is a hollow tube, the upper end of the tube body is movably connected with the arc joint through thread, and the middle and upper part of the tube body is opened with a rectangular slot, the rotating rod is inserted in the tube body, and the spiral rotating piece is sleeved on the periphery of the rotating rod. However, the above-mentioned thrombus removal device is complicated in structure, high in preparation cost, and cumbersome to use, and when the thrombus on the blood vessel wall is peeled off by the rotation of the spiral cutter or the spiral rotating piece in the blood vessel, it is easy to damage the blood vessel endothelium, which may easily lead to the occurrence of sequelae of thrombus removal.

Another example is the AngioJet thrombus removal device, which can spray a certain amount of thrombolytic agent into the thrombus under high pressure to break the thrombus, and increase the contact area with the thrombus, and then perform thrombus aspiration (it can be called chemical and physical coupling thrombus volume reduction), suitable for acute thrombosis of iliac, femoral and popliteal veins. However, too long a negative pressure time often causes the patient to lose too much blood, and at the same time, high-pressure rapid stirring may cause red blood cell damage and hemolysis which may easily lead to sequelae of thrombus removal.

SUMMARY OF THE INVENTION

The technical problem to be solved by the present disclosure is to provide a thrombus treatment platform that can reduce the occurrence of sequelae of thrombus removal.

To solve the above technical problems, the present disclosure employs the following technical solution:

From the perspective of the product structure, the thrombus treatment platform of the present disclosure comprises an aspiration catheter with an aspiration channel, and the thrombus treatment platform further comprises an aspiration pump that communicate with the proximal end of the aspiration catheter, a stirring device, and a filter assembly, The filter assembly comprises a filter rod, and a filter screen fixedly mounted at the distal end of the filter rod and having an expanded state and a collapsed state;

The stirring device comprises a first catheter, a second catheter sliding sleeved outside the first catheter, a stirrer arranged at the distal end of the first catheter and having an expanded state and a collapsed state, and an operating device arranged between the first catheter and the second catheter and capable of causing the first catheter and the second catheter to slide relatively so that the stirrer can be switched between the expanded state and the collapsed state;

The thrombus treatment platform further comprises a driving device connected with the first catheter or the second catheter and capable of driving the rotation of the stirrer.

From the perspective of the use of state of the product, the thrombus treatment platform of the present disclosure comprises an aspiration catheter with an aspiration channel, and the thrombus treatment platform further comprises an aspiration pump that communicate with the proximal end of the aspiration catheter, a stirring device, and a filter assembly, The filter assembly comprises a filter rod passing through the aspiration channel, and a filter screen fixedly mounted at the distal end of the filter rod and having an expanded state and a collapsed state; the filter screen is located at the distal end of the aspiration catheter;

The stirring device comprises a first catheter passing through the aspiration channel, a second catheter passing through the aspiration channel and sliding sleeved outside the first catheter, a stirrer arranged at the distal end of the first catheter and having an expanded state and a collapsed state, and an operating device arranged between the first catheter and the second catheter and capable of causing the first catheter and the second catheter to slide relatively so that the stirrer can be switched between the expanded state and the collapsed state; when the stirrer is in the expanded state, the stirrer is located between the filter screen and the distal end of the aspiration catheter, and when the first catheter is dragged, the stirrer is moved back and forth in the blood vessel;

The thrombus treatment platform further comprises a driving device connected with the first catheter or the second catheter and capable of driving the rotation of the stirrer.

When the present disclosure is in use, by arranging the filter assembly downstream of the blood flow, thrombus can be prevented from flowing into other sites along the blood flow; and by inletting thrombolytic drugs, and dragging the stirring device back and forth to make the stirrer move back and forth in the blood vessel, the stirrer scrapes the blood vessel wall back and forth and stirs the thrombus in the blood vessel, or through a driving device, the stirrer is driven to rotate to break the thrombus, or through ultrasonic turbulence, the thrombus falling off from the blood vessel wall, the thrombus breaking and the thrombus capturing are achieved; and with the aspiration catheter to aspirate thrombus, a large number of deep vein thrombus and old thrombus can be quickly removed without damaging the blood vessel wall and venous valve, reducing the sequelae of thrombus removal.

The aspiration catheter of the present disclosure can also provide access to other thrombus removal devices on the premise that it has the function of thrombus removal, thereby facilitating doctors to select surgical schemes for different thrombus, thereby making this thrombus treatment platform applicable to a wide range of indications.

Of course, for some thrombotic diseases that can be treated only by aspirating through the aspiration catheter, the medical staff can only use the aspiration catheter of the present disclosure without using the stirring device and the filter assembly.

In the present disclosure, the aspiration catheter, the filter assembly, the stirring device, the sheathing canal, the driving device, and the aspiration pump are individually packaged, these individually packaged components can be sold as a whole or separately, so as to facilitate the selective use by medical staff. Of course, the aspiration catheter, the filter assembly, the stirring device, the sheathing canal, the driving device, and the aspiration pump can also be sold in one package.

According to one embodiment, the thrombus treatment platform further comprises a guide wire. This product can be sold together with guide wires, or guide wires from other manufacturers can be used.

Due to the implementation of the above technical solutions, the present disclosure has the following advantages over the prior art:

The present disclosure can remove thrombus under the condition of ensuring relative safety, and is particularly suitable for removing a large number of thrombus in the inferior vena cava, protects venous valves and venous vessel walls, has controllable blood loss and simple operation steps, shortens operation time, and reduces patient hospitalization expenses.

BRIEF DESCRIPTION OF THE DRAWINGS

FIG. 4 is a schematic diagram of the aspiration catheter of Embodiment 1 bent at 0° and 30°;

FIG. 5 is a schematic diagram of partial section of the aspiration catheter of Embodiment 2;

FIG. 6 is a partial enlarged view of FIG. 5;

FIG. 7 is a schematic cross-sectional view of FIG. 5;

FIG. 8 is a schematic diagram of the aspiration catheter of Embodiment 2 bent at ±30°;

FIG. 9 is a schematic structure diagram of the aspiration catheter of Embodiment 3;

FIG. 13 is a schematic diagram of the aspiration catheter of Embodiment 3 bent at ±30° in a plane;

FIG. 14 is a schematic structure diagram of the filter assembly with a basket filter;

FIG. 15 is a schematic structure diagram of the filter assembly with a shuttle filter;

FIG. 16 is a schematic structure diagram of the filter assembly with a pocket filter;

FIG. 17 is a schematic structure diagram of the stirring device of Embodiment 5 when it is in the collapsed state;

FIG. 18 is a schematic structure diagram of the stirring device of Embodiment 5 when it is in the expanded state;

FIG. 19 is an enlarged view of Part A of FIG. 18;

FIG. 20 is a schematic structure diagram of the stirring device of Embodiment 6 when it is in the collapsed state;

FIG. 21 is a schematic structure diagram of the stirring device of Embodiment 6 when it is in the expanded state;

FIG. 22 is a cross-sectional view alone Line A-A of FIG. 21;

FIG. 23 is an enlarged view of Part B of FIG. 21;

FIG. 24 is a cross-sectional view alone Line C-C of FIG. 23;

FIG. 25 is a partial cross-sectional view of the stilling assembly with the operation assembly in the locked state and the stirrer in the collapsed state (the stirring device does not have an ultrasonic function);

FIG. 26 is a partial cross-sectional view of the stirring assembly with the operation assembly in the locked state and the stirrer in the expanded state (the stirring device does not have an ultrasonic function);

FIG. 27 is a partial cross-sectional view of the operation assembly in the unlocked state and the lock assembly in the locked state (the stirring device does not have an ultrasonic function);

FIG. 32 is a schematic structure diagram of the dilator;

FIG. 33 is a schematic structure diagram of the sheathing canal;

FIG. 34 is a cross-sectional view alone Line A-A of FIG. 33;

FIG. 35 is a state diagram when the sheathing canal transports the filter assembly;

FIG. 41 is a state diagram of the aspiration catheter (excluding the ultrasonic generator) and the stirring device (including the ultrasonic generator) when they cooperate with the filter assembly (the driving device is omitted and not shown);

FIG. 42 is a state diagram of the aspiration catheter (including the dilating catheter) and the stirring device (including the ultrasonic generator) when they cooperate with the filter assembly (the driving device is omitted and not shown);

FIG. 43 is a state diagram of the aspiration catheter (including the ultrasonic generator) and the stirring device (including the ultrasonic generator) when they cooperate with the filter assembly (the driving device is omitted and not shown);

DETAILED DESCRIPTION OF EXEMPLARY EMBODIMENTS

Figure 1:
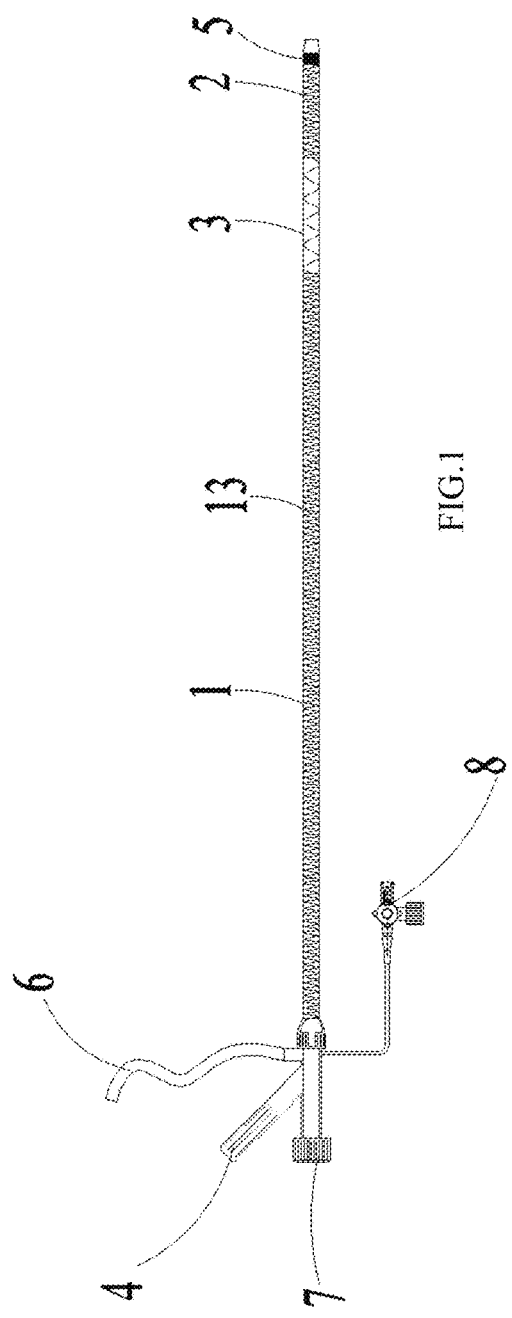
FIG. 1 is a schematic structure diagram of the aspiration catheter of Embodiment 1 and Embodiment 2.

In the following, the present disclosure is further described combining with embodiments. However, the present disclosure is not limited by the following embodiments. The implementation conditions employed by the embodiments may be further adjusted according to different requirements of specific use, and undefined implementation conditions usually are conditions in this industry. The technical features involved in the various implementations of the present disclosure may be combined with each other as long as they do not conflict with each other. In the following, only certain exemplary embodiments are briefly described. As those skilled in the art can realize, the described embodiments may be modified in various different ways without departing from the spirit or scope of the embodiments of the present disclosure. Therefore, the drawings and description are to be regarded as illustrative in nature and not restrictive.

In the description of embodiments of the present disclosure, it should be understood that the proximal end herein is defined as the side close to the medical staff when the platform for management of thrombosis is used; the distal end is defined as the side away from the medical staff when the platform for management of thrombosis is used. The definitions of various orientations are only for the convenience of describing the embodiments of the present disclosure and simplifying the descriptions, rather than indicating or implying that the specified device or element must have a specific orientation, be configured and operated in a specific orientation, and therefore cannot be understood as a limitation to the embodiments of the present disclosure.

In the embodiments of the present disclosure, unless otherwise clearly specified and defined, the terms "connect", "connecting", "fix", "fixing" and other terms should be understood in a broad sense, for example, it may be a fixed connection, it can be a detachable connection, or integrated; it can be a mechanical connection, it can be an electrical connection, or it can be in communication; it can be directly connected, or indirectly connected through an intermediate medium, it can be an internal communication between two elements or an interaction relationship between two elements. For those of ordinary skill in the art, the specific meanings of the above-mentioned terms in the embodiments of the present disclosure can be understood according to specific conditions.

In the embodiments of the present disclosure, unless otherwise clearly specified and defined, the "above" or "under" of the first feature on the second feature may include that the fast and second features are in direct contact, or may include that the first and second features are not in direct contact but through another feature between them. Moreover, the first feature "on", "above" and "over" the second feature include the first feature being directly above and obliquely above the second feature, or it simply means that the first feature has a higher level than the second feature. The first feature "under", "below", and "underneath" the second feature include the first feature directly above and diagonally above the second feature, or it simply means that the first feature has a smaller level than the second feature.

The following disclosure provides many different implementations or examples for implementing different structures of the embodiments of the present disclosure. In order to simplify the disclosure of the embodiments of the present disclosure, the components and configurations of specific examples are described below. Of course, they are only examples, and are not intended to limit the embodiments of the present disclosure. In addition, the embodiments of the present disclosure may repeat reference numerals and/or reference letters in different examples, such repetition is for the purpose of simplification and clarity, and does not indicate the relationship between the various implementations and/or configurations discussed.

The thrombus treatment platform of the present disclosure comprises an aspiration catheter 10 with an aspiration channel, an aspiration pump 19, a stirring device, and a filter assembly, etc.

FIG. 1 to FIG. 13 are schematic structure diagrams of the aspiration catheter 10 of Embodiment 1 to Embodiment 3, and FIG. 28 to FIG. 31 are schematic structure diagrams of the aspiration catheter 10 of Embodiment 4. The aspiration catheter 10 comprises a catheter part with an aspiration channel, the aspiration channel extends along the axial direction of the catheter part and runs through the catheter part, and the outer diameter of the catheter part is 12 to 14 F.

As shown in FIGS. 5 and 6, the catheter part comprises a first wall layer 11 located on the inner side, a second wall layer 12 located on the outer side, and a support 13 arranged between the first wall layer 11 and the second wall layer 12, the support 13 comprises a plurality of repeats continuously arranged along the axial direction of the catheter part, wherein the spacing between the repeats of the support 13 varies from the proximal end to the distal end, so that the catheter part is divided into a first tube portion 1 at the proximal end, a second tube portion 2 at the distal end, and a third tube portion 3 between the first tube portion 1 and the second like portion 2, and the spacing between two adjacent repeats at the position of the first tube portion 1 and the spacing between two adjacent repeats at the position of the tube portion 2 is smaller than the spacing between two adjacent repeats at the position of the third tube portion 3, so that the hardness of the third tube portion 3 is less than that of the first tube portion 1 and the second tube portion 2, and the bending of the second tube portion 2 relative to the first tube portion 1 can be better realized.

According to some implementations, the front end of the catheter part can be directionally bent at 0 to 180°, preferably at 0 to 90°, and more preferably at 0 to 30°.

Wherein the support 13 composed of the plurality of repeats can be spring-like spiral or accordion-like structure, when the support 13 is spiral, the spacing of the repeats is the pitch, and when the support 13 is an accordion structure, the spacing of the repeats is the distance between two adjacent peaks. In this embodiment, the support 13 preferably adopts a spiral shape.

As for the bending angle of the second tube portion 2 relative to the first tube portion 1, it can be achieved by adjusting the spacing of the repeats and the material of the catheter part, in this embodiment, the material of the support 13 is selected from metal, such as 304 stainless steel or nickel-titanium alloy wire, etc.; the first wall layer 11 and the second wall layer 12 are made of polytetrafluoroethylene (PTFE), block polyetheramide (Pcbax) polyimide (PI), polyamide (PA), polyethylene (PE), metal film, etc. Preferably, the first wall layer 11 is made of polytetrafluoroethylene (PTFE) with better lubricity to facilitate the passage of thrombus through the aspiration channel, and the second wall layer 12 is made of block polyetheramide (Pcbax) or metal film, etc., and the second wall layers 12 of the first tube portion 1, the second tube portion 2 and the third tube portion 3 can be spliced with different materials.

The aspiration catheter 10 further comprises a fixing piece 15 fixedly arranged at the far end of the third tube portion 3 of the catheter part, the fixing piece 15 in this embodiment is a developing ring, and using the developing ring as the fixing piece 15 can facilitate the operator to understand the location of the distal end of the aspiration catheter 10 while realizing the fixed connection of a connecting piece 14 with the catheter part (which will be described in detail below). For the solutions of Embodiments 1 to 3, the developing ring is fixed between the first wall layer 11 and the second wall layer 12 by means of hot melting or welding.

The aspiration catheter 10 further comprises a connecting piece 14 fixedly connected to the fixing piece 15 at the distal end thereof, and an operating portion 4 movably connected to the proximal end of the catheter part, and the proximal end of the connecting piece 14 is connected to the operating portion 4. The connecting piece 14 is located between the first wall layer 11 and the second wall layer 12 and extends along the axial direction of the catheter part, so that the axis line of the connecting piece 14 is parallel to and does not overlap with the axis line of the catheter part, thereby making the connecting piece 14 can drive the second tube portion 2 to bend.

In this implementation, the operating portion 4 is operated by the medical staff, so that the movement of the operating portion 4 drives the movement of the connecting piece 14, and the connecting piece 14 further pulls the fixing piece 15 to bend the catheter part, so that there is an angular deviation between the distal end of the catheter part and the proximal end of the catheter part, thereby facilitating the adjustment of the angle of the head of the aspiration catheter according to clinical needs, for example, it can be easily inserted into bifurcated blood vessels.

The connecting piece 14 and the fixing piece 15 can be fixedly connected by knotting, hot melting or welding, etc. The connecting piece 14 is a metal wire, such as 304 stainless steel wire, nickel-titanium alloy wire, and the like.

In this implementation, the movable connection between the operating portion 4 and the catheter part can be a sliding connection or a rotating connection, however, for the sliding connection, the operating portion 4 needs to move a certain distance in the axial direction of the aspiration catheter 10, so that it is inconvenient for medical staff to operate, and also increases the volume of the aspiration catheter 10, therefore, preferably, the operating portion 4 is rotationally connected to the catheter part, and the proximal end of the connecting piece 14 is arranged around the operating portion 4, so that the length of the connecting piece between the operating portion 4 and the liking piece 15 can be extended or shortened by rotating the operating portion 4 forward or reversely, so as to realize the bending of the distal end of the catheter part.

Figure 2:
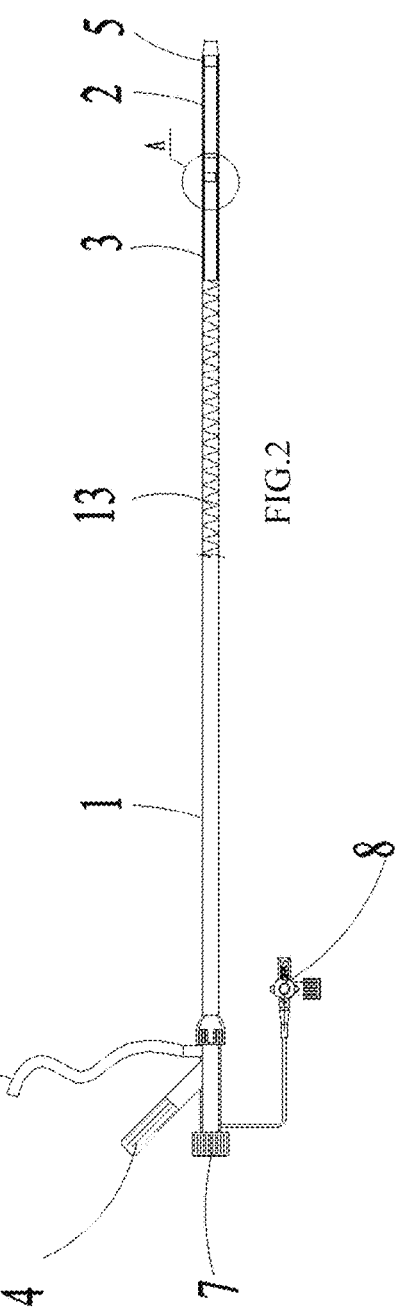
FIG. 2 is a schematic diagram of partial section of the aspiration catheter of Embodiment 1.
Figure 3:
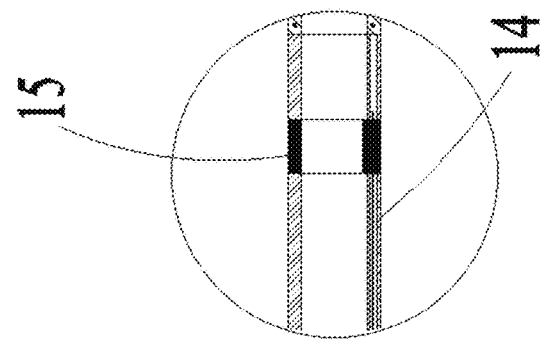
FIG. 3 is a partial enlarged view of FIG. 2.
Figure 10:
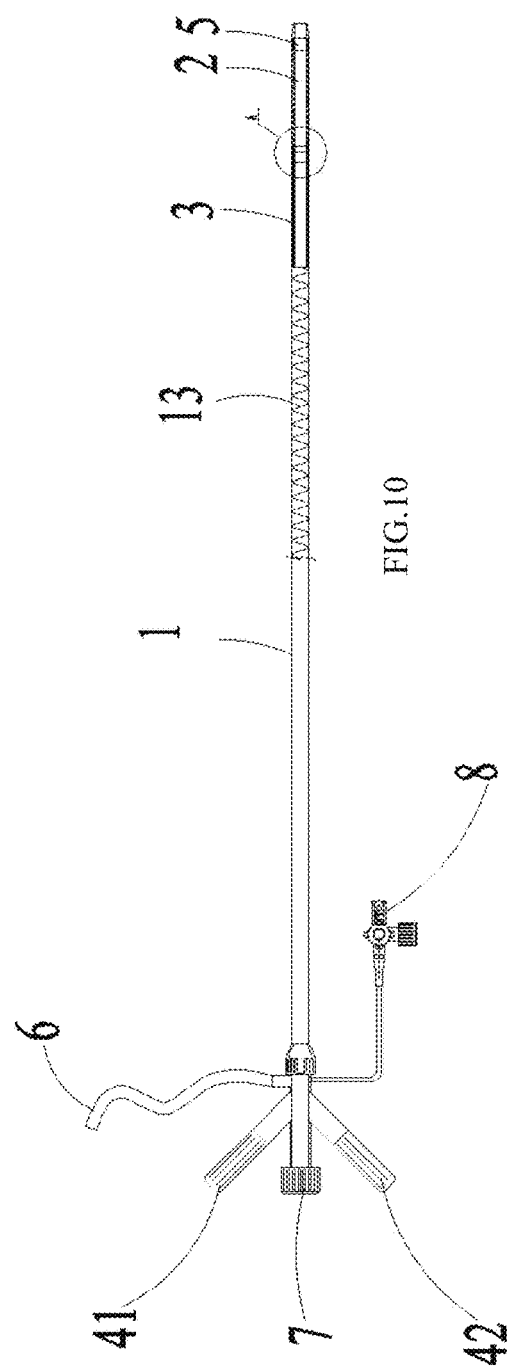
FIG. 10 is a schematic diagram of partial section of the aspiration catheter of Embodiment 3.
Figure 11:
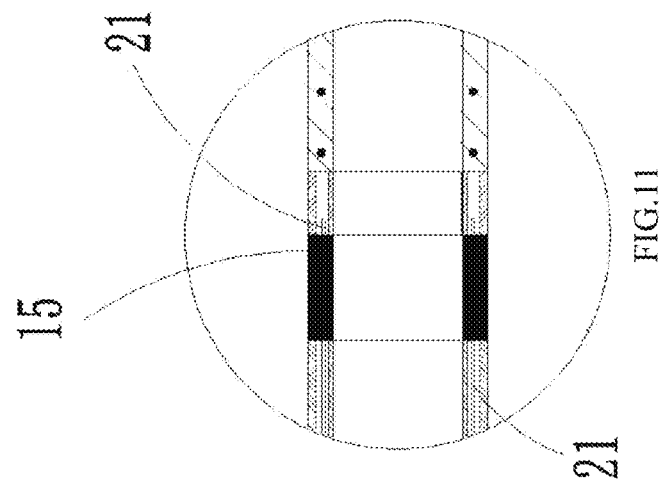
FIG. 11 is a partial enlarged view of FIG. 10.
Figure 12:
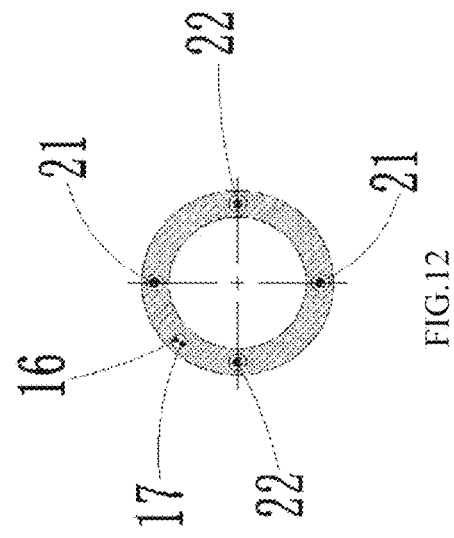
FIG. 12 is a schematic cross-sectional view of FIG. 10.
Figure 28:
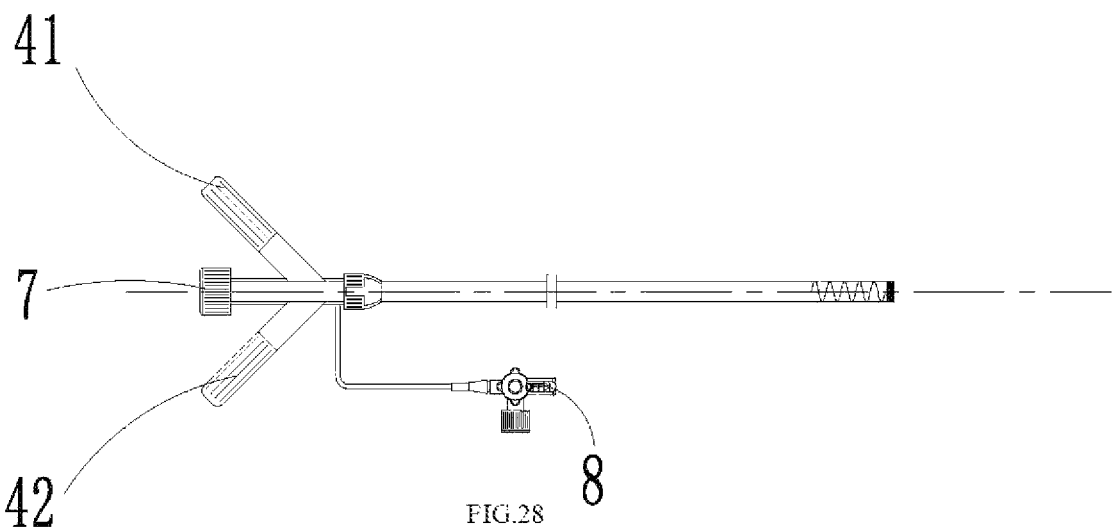
FIG. 28 is a schematic structure diagram of the aspiration catheter of Embodiment 4 (the dilating catheter is in the collapsed state)
Figure 29:
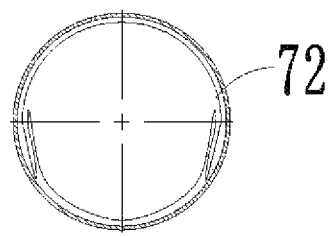
FIG. 29 is a cross-sectional view of the dilating catheter of Embodiment 4 when it is in the collapsed state.
Figure 30:
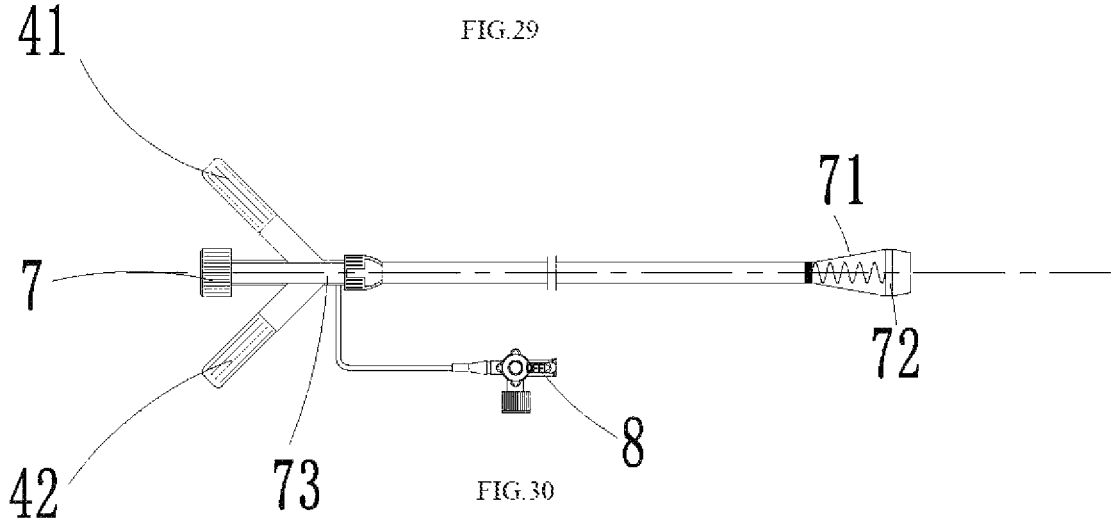
FIG. 30 is a schematic structure diagram of the aspiration catheter of Embodiment 4 (the dilating catheter is in the expanded state)
Figure 31:
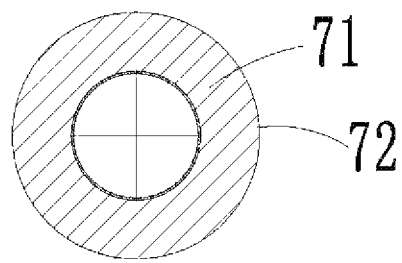
FIG. 31 is a cross-sectional view of the dilating catheter of Embodiment 4 when it is in the expanded state.
Figure 36:
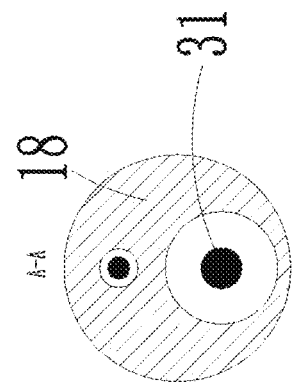
FIG. 36 is a cross-sectional view alone Line A-A of FIG. 35.

As shown in FIGS. 1, 2 and 7, the aspiration catheter 10 further comprises a second ultrasonic generator 5 arranged at the distal end of the catheter part (that is, the position at the distal end of the second tube portion 2), a second power line 16 and a second signal transmission line 17 connected with the second ultrasonic generator 5 and arranged in the wall of the catheter part (i.e., between the first wall layer 11 and the second wall layer 12), a second ultrasonic connector 6 arranged at the proximal end of the catheter part and connected to the second power line 16 and the second signal transmission line 17, and the second ultrasonic connector 6 may be connected to other devices.

FIGS. 1 to 4 show Embodiment 1, where the connecting piece 14 is only one steel wire, and the distal end of the connecting piece 14 is fixedly connected to the developing ring, and the proximal end is wound around the operating portion 4, at this time, there is only one connection point between the connecting piece 14 and the developing ring, therefore, when the operating portion 4 is rotated, the catheter part can only be bent in a single direction, and the angle range that can be bent is 0 to 90°, the angle range shown in FIG. 4 is 0° and 30°.

FIGS. 1, 5 to 8 show Embodiment 2, where the connecting piece 14 is also one steel wire, but the two end portions of the connecting piece 14 (that is, the distal ends of the connecting piece 14) are respectively fixedly connected to opposite sides of the fixing piece 15, and the middle position of the connecting piece 14 is wound on the operating portion 4, so that the connecting piece 14 is divided into two parts by the operating portion 4, here, the upper and lower portions are used to describe, for example, when the operating portion 4 is rotated clockwise, the upper connecting piece 14 is elongated, the lower connecting piece 14 is correspondingly shortened, and the second tube portion 2 of the catheter part is rotated downward by a certain angle; when the operating portion 4 is rotated counterclockwise, the upper connecting piece 14 is shortened, the lower connecting piece 14 is correspondingly elongated, and the second tube portion 2 of the catheter part is rotated upward by a certain angle. The description here assumes that the second tube portion 2 is located on the same straight line as the first tube portion 1 and the third tube portion 3, that is, it is described that the bending angle of the second tube portion 2 is 0° as the starting position. Therefore, the catheter part of Embodiment 2 can be bent in both directions, and can be bent in the range of 0 to 90° in both directions, and the angle ranges shown in FIG. 8 are 0° and ±30°. Of course, the connecting piece 14 in Embodiment 2 can also be two steel wires, the distal ends of the two steel wires are respectively fixedly connected to opposite sides of the fixing piece 15, and the proximal ends are respectively wound on the operating portion 4 in opposite winding directions, which can achieve the effect similar to one steel wire driving the bending of the catheter part.

FIGS. 9 to 13 show Embodiment 3, in which the operating portion comprises a first operating portion 41 movably connected to the proximal end of the catheter part, and a second operating portion 42 movably connected to the proximal end of the catheter part, the connecting piece comprises a first connecting piece 21 that is wound around the first operating portion 41, and a second connecting piece 22 that is wound around the second operating portion 42, the two distal ends of the first connecting piece 21 are respectively arranged on opposite sides of the fixing piece 15, the two distal ends of the second connecting piece 22 are respectively arranged on the opposite sides of the fixing piece 15, and the two distal ends of the first connecting piece 21 and the two distal ends of the second connecting piece 22 are evenly distributed in the circumferential direction of the fixing piece 15, so that by operating the first operating portion 41 and the second operating portion 42 at the same time, the tip end of the catheter part can be rotated by 360°. That is, the solution of Embodiment 3 is equivalent to the solution of Embodiment 2 by adding a set of operating portions and connecting pieces. Of course, the first connecting piece 21 and the second connecting piece 22 in Embodiment 3 may also be two steel wires, respectively, and the connection mode can refer to the connection manner of the two steel wires in Embodiment 2, which will not be repeated here.

The operating portion 4 of Embodiments 1 to 3 may be arranged at the proximal end of the catheter part, or at the proximal side of the catheter part, preferably on the proximal side of the catheter part, so as to facilitate the mounting of the hemostatic valve 7 at the proximal end of the catheter part. For Embodiment 3, the first operating portion 41 and the second operating portion 42 are located on two sides of the catheter part, so that the layout of a handle 54 of the aspiration catheter 10 is more reasonable.

FIG. 28 to FIG. 31 show schematic structure diagram of the aspiration catheter 10 of Embodiment 4, its structure is to add a dilating catheter on the basis of Embodiments 1 to 3, and its specific structure is as follows:

The aspiration catheter 10 further comprises a dilating catheter connected to the distal end of the catheter part and having an expanded state and a collapsed state, and when the dilating catheter is in the collapsed state, the dilating catheter is located within the catheter part; when the dilating catheter is in the expanded state, the dilating catheter is located outside the catheter part, and the diameter of the distal end of the dilating catheter is larger than the diameter of the catheter part. Wherein, the dilating catheter is described in the position when the dilating catheter is in the expanded state. The dilating catheter comprises a soft membrane 71 fixedly connected to the distal end of the catheter part at its proximal end, and a dilating ring 72 fixedly connected to the distal end of the soft membrane 71. The dilating ring 72 may be a memory material or a balloon that can keep the distal end of the dilating catheter in an expanded state; when a memory material is used, it can be a self-expanding memory material or a memory material that needs to be expanded by a dilator, the memory material can be nickel-titanium material, etc., in this case, the material of the soft membrane 71 is PTFE (polytetrafluoroethylene) or ePTFE (polytetrafluoroethylene microporous membrane); when a balloon is used, the aspiration catheter 10 further comprises a channel for inflating and deflating the balloon, in this case, the soft membrane 71 may be a latex elastic polymer material with biocompatibility. When a aspiration catheter 10 with a dilating catheter at the distal end is used, the outer diameter of the catheter part can be 12 F; and the outer diameter of the dilating catheter after expansion can reach 14 F, so that the aspiration catheter 10 can be more conveniently inserted into and withdrawn from the human body, and can be adapted to more blood vessels.

The structure of the catheter part of the aspiration catheter 10 can refer to the structure of the catheter part of Embodiment 1, wherein the first wall layer 11 and the second wall layer 12 may slide relatively, and the proximal ends of the soft membrane 71 of the dilating catheter are fixedly connected to the distal end of the first wall layer 11 and the distal end of the second wall layer 12, respectively, so that when the dilating catheter needs to be expanded, the first wall layer 11 may be moved distally to push the dilating catheter out of the catheter part, and when the dilating catheter needs to be retracted, the first wall layer 11 may be moved proximally so that the dilating catheter can be received within the catheter part. Wherein, the first wall layer 11 and the second wall layer 12 need to have good flexibility and anti-curling property, and the material of the first wall layer 11 and the second wall layer 12 is preferably a soft material film such as ePTFE, PTFE, etc., and the structure of the support 13 and the like is the same as that of Embodiments 1 to 3.

Since the first wall layer 11 and the second wall layer 12 of this embodiment may slide relatively, the fixing piece 15 is preferably fixed on the second wall layer 12.

In this embodiment, the aspiration catheter 10 further comprises a handle 73 fixedly connected to the first wall layer 11, and the handle 73 is rotatably connected to the second wall layer 12, so that by rotating the handle 73, the first wall layer 11 may be driven to rotate relative to the second wall layer 12 and move in the axial direction, so that the dilating catheter may be pushed out and retracted. The hemostatic valve 7, the first operating portion 41, and the second operating portion 41 are mounted on the handle 73, and a three-way valve 8 is mounted on the handle 73 and communicates with the internal cavity of the first wall layer 11.

In the above embodiment, the bending direction and bending angle of the tip of the catheter part are precisely controlled by rotating the operating portion 4, for example, the diameter of the operating portion 4 can be adjusted by calculation, so that every time the operating portion 4 is rotated by a round, the tip of the catheter part may be bent at a certain angle, such as 1°, 2°, 3°, etc., of course, in order to avoid excessive work intensity of the medical staff, the bending angle of the catheter part caused by rotating the operating portion 4 by a round may be set to 5° and so on.

The aspiration catheter 10 in the above embodiment further comprises a three-way valve 8 communicating with the proximal end of the catheter part. The medical staff can pass physiological saline, thrombolytic agents, etc., to the catheter part through the three-way valve 8, or connect the aspiration pump 19 through the three-way valve 8 to aspirate the thrombus.

In the above embodiment, the operating portion 4 is operated by an operator, so that the movement of the operating portion 4 drives the movement of the connecting piece 14, and the connecting piece 14 further pulls the catheter wall to bend the catheter part, so that there is an angular deviation between the distal end of the catheter part and the proximal end of the catheter part, thereby facilitating the adjustment of the angle of the head of the aspiration catheter 10 according to clinical needs, for example, when used as the aspiration catheter 10 to enter a blood vessel, by adjusting the angle of the tip, it can be easily inserted into bifurcated blood vessels.

FIGS. 14 to 16 show three filter assemblies with different structures, and all of the three filter assemblies can be used with the aspiration catheter 10 of the above four embodiments.

The filter assembly comprises a filter rod 31, and a filter screen 32 fixedly mounted at the distal end of the filter rod 31 and having an expanded state and a collapsed state. The filter screen 32 shown in FIG. 14 is in the shape of a basket with an opening toward the proximal end, the filter screen 32 shown in FIG. 15 is in the shape of a shuttle, and the filter screen 32 shown in FIG. 16 is in the shape of a pocket with an opening toward the proximal end.

The outer diameter of the filter rod 31 is 0.1 to 1 mm, preferably 0.035 in, so that the filter rod 31 may be used as a guide wire, and it is convenient for other components to enter the desired position along the filter rod 31.

FIGS. 33 and 34 are schematic structural diagrams of the sheathing canal 18, where the sheathing canal 18 comprises a first channel 181 for the passage of a guide wire and a second channel 182 that can allow thrombus to pass through or can receive the filter screen 32. In use, the sheathing canal 18 can pass through the aspiration channel and extend its distal end to the proximal end of the filter screen 32, the proximal end of the sheathing canal 18 is connected with an aspiration pump 19, wherein the aspiration pump 19 and the aspiration pumps 19 connected with the aspiration catheter 10 may be the same or different.

The way the filter assembly enters the blood vessel and extends to the distal end of the thrombus may adopt conventional methods in the prior art, for example, by loading the filter assembly in the sheathing canal 18 and then inserting the sheathing canal 18 along the guide wire into a desired position. The filter screen 32 can be loaded within the sheathing canal 18 in the collapsed state, and in the expanded state, the outer diameter of the filter screen 32 (that is, the maximum distance of the cross-section after the filter screen 32 bulges) is greater than or equal to the inner diameter of the blood vessel, thereby making the filter screen 32 can filter thrombus passing through the filter screen 32 well to prevent the thrombus from flowing to other sites.

The stirring device comprises a first catheter 51, a second catheter 52 sliding sleeved outside the first catheter 51, a stirrer 53 arranged at the distal end of the first catheter 51 and having an expanded state and a collapsed state, and an operating device arranged between the first catheter 51 and the second catheter 52 and capable of causing the first catheter 51 and the second catheter 52 to slide relatively so that the stirrer 53 can be switched between the expanded state and the collapsed state. The thrombus treatment platform further comprises a driving device connected with the first catheter 51 and/or the second catheter 52 and capable of driving the rotation of the stirrer 53.

The driving device comprises a motor 20 connected to the first catheter 51 or the second catheter 52, and a power source capable of powering the motor 20, wherein, the power source may be a dry battery or a power line that may be connected to an external power source.

Wherein, the stirrer 53 is a basket woven by a plurality of wires 56, and the two ends of each wire 56 are respectively located at the proximal end and the distal end of the first catheter 51, that is, the axial direction of each wire 56 approximately extends along the axial direction of the first catheter 51, but at least part of the wires 56 rotates around the first catheter 51 at a certain angle and at least part of the wires 56 intersect, the specific angle may be set based on the length of the wires, the maximum outer diameter required when the stirrer is in the expanded state, and the density and size of the basket to be woven. The material of the wires 56 is nickel-titanium alloy, stainless steel wire, high molecular polymer, etc. When the stirrer 53 is in the collapsed state, the outer diameter of the stirrer 53 is ≤6 F. and further preferably, the outer diameter of the stirrer 53 is ≤5.5 F, more preferably ≤5 F.

The degree of expansion of the stirrer 53 may be controlled by the first catheter 51 and/or the second catheter 52, so that medical staff may control the distance and the degree of adhesion between the stirrer 53 and the blood vessel wall according to actual needs, which is more convenient to use; the stirrer 53 in this implementation is braided by a silk threads 56, and when in the collapsed state, the outer diameter is very small, so that the size of the second catheter 52 may be reduced, leaving a larger space for the aspiration channel, and improving the efficiency of thrombus aspiration.

FIGS. 17 to 19 are an implementation of the stirring device of Embodiment 5, wherein the distal end of the first catheter 51 extends out of the second catheter 52; the distal end of each wire 56 is fixedly connected to the first catheter 51, and the proximal end is fixedly connected to the second catheter 52; when the first catheter 51 is moved toward the proximal end relative to the second catheter 52, the stirrer 53 is expanded, and as the first catheter 51 moves longer, the degree of expansion of the stirrer 53 is greater, the outer diameter of the stirrer 53 is larger, as shown in FIG. 18; when the first catheter 51 is moved toward the distal end relative to the second catheter 52 until the wire 56 is straightened, the stirrer 53 is in a collapsed state, and at this time, the outer diameter of the stirrer 53 is the smallest, and it is basically attached to the first catheter 51, as shown in FIG. 17, the outer diameter of the stirrer 53 can be 5 F at this time. In the above Embodiment 5, the structure of the operating device is shown in FIGS. 25 to 27: the operating device comprises a handle 54 sleeved on the first catheter 51 and the second catheter 52, a locking assembly provided between the first catheter 51 and the second catheter 52 and capable of locking the two relative to each other, and an operating assembly that is slidably connected to the handle 54 and capable of being locked in cooperation with the first catheter 51. The first catheter 51 passes through the handle 54 and protrudes from the proximal end of the handle 54.

The locking assembly comprises a first locking member 60, a second locking member 61, a third locking member 62, and the like.

The first locking member 60 is fixedly connected to the distal end of the second catheter 52, wherein, the first locking member 60 and the second catheter 52 may be fixedly connected by hot melting, welding, etc., or may be integrated by extrusion molding or injection molding. An external thread is formed on the outer surface of the first locking member 60.

The distal end of the handle 54 is provided with an accommodating groove capable of accommodating the second locking member 61, the second locking member 61 may rotate in the accommodating groove, and a plurality of protruding ribs are formed on the outer surface of the second looking member 61, and these protruding ribs may increase the friction of the outer surface of the second locking member 61, thereby facilitating the rotation of the second locking member 61 to realize the locking and unlocking of the locking assembly. The second locking member 61 is sleeved on the first catheter 51 and may rotate around the first catheter 51, a groove is formed on the second locking member 61, and an internal thread is formed on the wall of the groove.

The first locking member 60 is inserted in the groove of the second locking member 61, and the first locking member 60 and the second locking member 61 are rotatably connected by the internal thread and the external thread, so that the distance from the proximal end of the first locking member 60 to the bottom of the groove may be adjusted, and a cavity is formed between the proximal end of the first locking member 60 and the bottom of the groove, and the third locking member 62 is located in this cavity.

The material of the third locking member 62 is a material that may be elastically deformed, such as silica gel.

When the locking assembly is in the unlocked state, the third locking member 62 is in a natural state, at this time, although the third locking member 62 is still in contact with the first locking member 60, the second locking member 61 and the first catheter 51, their tightness of cooperation is not high, at this time, when an external force applied to the first catheter 51 is greater than the friction between the third locking member 62 and the first catheter 51, the first catheter 51 and the second catheter 52 may slide relatively.

When the locking assembly needs to be locked, the second locking member 61 is rotated to make the second locking member 61 move distally so that the cavity between the first locking member 60 and the second locking member 61 becomes smaller, at this time, the third locking member 62 is squeezed and elastically deformed, so that the third locking member 62 is more closely cooperated with the first locking member 60, the second locking member 61, and the first catheter 51, at this time, the friction between the third locking member 62 and the first catheter 51 is greatly increased, and the relative position of the first catheter 51 and the second catheter 52 is locked, and when the motor 20 drives the first catheter 51 to rotate around its own axis, the second catheter 52 will be rotated along with the first catheter 51, so that the stirrer 53 is rotated around its own axis to achieve the function of breaking the thrombus.

In order to make the locking assembly have the function of relatively locking the first catheter 51 and the second catheter 52, it also has a good sealing effect and may function as a hemostatic valve, and the locking assembly further comprises a gasket 63 arranged between the third locking member 62 and the first locking member 60.

The operating assembly comprises a sliding groove 57 opened on the handle 54 and extending in the proximal and distal direction, an operating member 55 inserted in the sliding groove 57 and slidably connected to the handle 54, a mating portion 64 formed on the operating member 55 and capable of mating with and locking in cooperation with the first catheter 51, a sliding rail 65 fixedly arranged on the inner wall of the handle 54, a sliding block 66 capable of sliding in cooperation with the sliding rail 65, and an elastic member 67 with two ends respectively arranged at the bottom of the mating portion 64 and the upper surface of the sliding block 66. Wherein, the elastic member 67 is a spring, and the number of the elastic members 67 is two arranged along the axial direction of the handle 54. Wherein, the arrangement of the sliding rail 65 can enable the elastic member 67 to smoothly slide along with the operating member 55 when the operating member 55 slides relative to the handle 54.

When the operating assembly is in the locked state, the upper surface of the mating portion 64 and the lower surface of the first catheter 51 are tightly mated and relatively locked under the elastic force of the elastic members 67, and when the locking assembly is in the unlocked state, by sliding the operating member 55 proximally, the first catheter 51 can be driven to slide proximally to expand the stirrer 53; otherwise, the stirrer 53 may be collapsed.

When the motor 20 is required to drive the stirrer 53 to rotate, the second locking member 61 is rotated to lock the locking assembly, and the operating member 55 is pressed down to overcome the elastic force of the elastic member 67, so that the mating portion 64 is separated from the first catheter 51 to cause the operating assembly to be in the unlocked state, at this time, the motor 20 starts to drive the first catheter 51 to rotate, and the rotation of the stirrer 53 can be realized.

FIGS. 20 to 24 show the stirring device of Embodiment 6, its structure is roughly similar to that of Embodiment 5, but on the basis of Embodiment 5, it has a function that it can emit ultrasonic waves to break thrombus, wherein, the stirring device further comprises a plurality of first ultrasonic generators 81 fixedly arranged on the wires 56, a first power line 82 connected to the first ultrasonic generators 81, and a first ultrasonic connector 84 that is provided on the operating device and can power the first power line 82. In this embodiment, the wires 56 have internal cavities, and the first catheter 51 or the second catheter 52 also has an internal cavity, the first power line 82 passes through the internal cavities of the wires 56 and the internal cavity of the first catheter 51 or the second catheter 52 to connect the first ultrasonic generators 81 and the first ultrasonic connector 84. For the solution where both ends of the wires 56 are fixed on the first catheter 51, the first power line 82 is passed through the wall of the first catheter 51; for the solution where the distal ends of the wires 56 are fixed on the first catheter 51 and the proximal ends are fixed on the second catheter 52, the first power lines 82 pass through the wall of the second catheter 52.

In this embodiment, the diameter of the first ultrasonic generators 81 is 0.2 to 0.4 mm, preferably 0.3 mm, the outer diameter of the wires 56 is 0.2 to 0.3 mm, preferably 0.25 mm, and the inner diameter of the wires 56 is 0.1 to 0.2 mm, preferably 0.15 mm.

The first ultrasonic generators 81 are fixed to the wires 56 by welding.

The structure of the operating device in this embodiment is basically the same as the operating device used in the stirrer of Embodiment 5, except for the connection between the first power line 82 and the first ultrasonic connectors 84.

Figure 47:
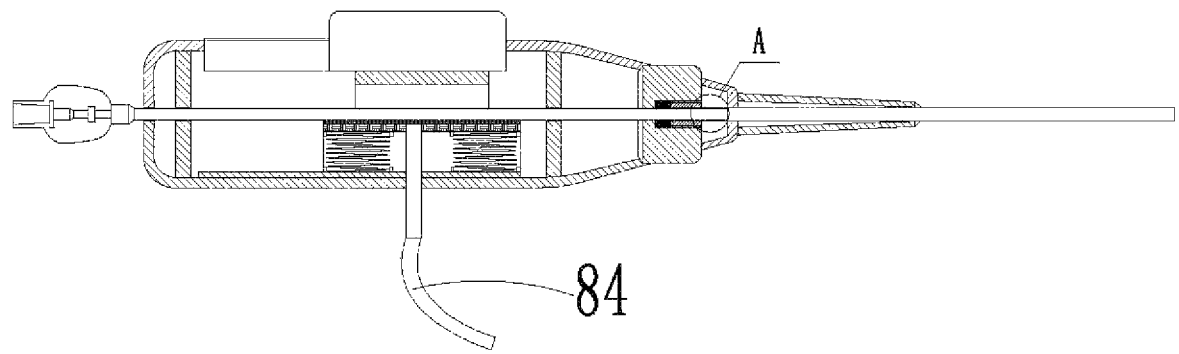
FIG. 47 is a partial cross-sectional view of the stilling assembly with the operation assembly in the locked state (the stirring device has an ultrasonic function)
Figure 48:
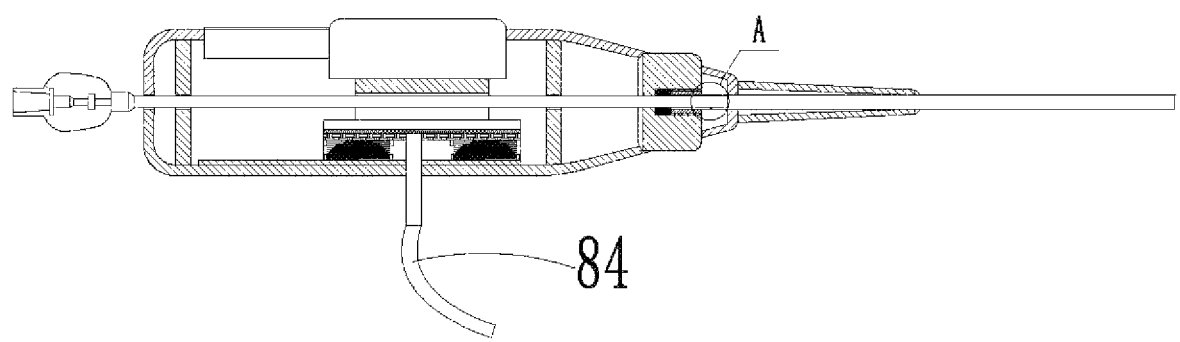
FIG. 48 is a partial cross-sectional view of the stilling assembly with the operation assembly in the locked state (the stirring device has an ultrasonic function)
Figure 49:
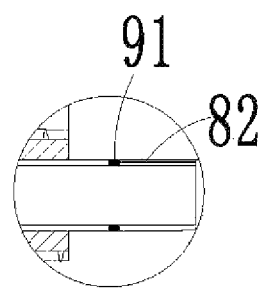
FIG. 49 is an enlarged view of Part A of FIG. 47 and FIG. 48.

Under this scheme, as shown in FIGS. 47 to 49, the first power line 82 is located in the inner cavity of the wires 56 and the inner cavity (i.e., the wall) of the second catheter 52; the stirring device further comprises a conductive ring 91 fixed arranged at the proximal end of the first power line 82; the conductive ring 91 is fixedly connected to the second catheter 52, and is slidably sleeved on the first catheter 51 and in contact with the first catheter 51; the first catheter 51 comprises a flexible tube section, a metal tube with the distal end fixedly connected to the proximal end of the flexible tube section, an insulating layer sleeved on the part of the metal tube, the material of the metal tube is stainless steel, etc.; the material of the mating portion 64 is conductive material, the first ultrasonic connector 84 is connected to the mating portion 64, and within the effective stroke of the relative movement of the first catheter 51 and the second catheter 52, the conductive ring 91 is in contact with the metal tube of the first catheter 51, and the mating portion 64 can contact the metal tube of the first catheter 51; when the mating portion 64 is in contact with the metal tube of the first catheter 51, the first ultrasonic connector 84 can supply power to the first ultrasonic generators 81.

In another implementation (not shown), distal and proximal ends of the plurality of wires are fixedly arranged on the first catheter, and the expansion and collapse of the stirrer and the degree of expansion of the stirrer are determined by how much the stirrer is received in the second catheter. When the stirrer is in the collapsed state, the stirrer is completely located in the second catheter; when the stirrer is in the expanded state, at least part of the stirrer is separated from the second catheter; when the stirrer is completely separated from the second catheter, the stirrer is expanded to the maximum state. This implementation may control the diameter of the stirrer after being collapsed by controlling the inner diameter of the second catheter.

In this implementation, the structure of the operating device may be the same as that of the above-mentioned embodiment, however, since the wires of the stirrer are all set on the first catheter, the second catheter may not be rotated together when the driving device drives the first catheter to rotate, therefore, the operating device in this implementation can omit the locking assembly, but the structure of the operating component can still be retained, and the structure of the operating component will not be repeated here; or the structure of the operating device can be very simple, including only one handle.

The stirrer 53 of the above two implementations can also be used with the aspiration catheter 10 shown in the above Embodiments 1 to 3.

In the above implementation, the stirring assembly also has the function of introducing thrombolytic drugs, the specific structure may be as shown in FIGS. 17 to 19. The first catheter 51 has a thrombolytic channel extending in the axial direction, the proximal end of the first catheter 51 is provided with an injection hole 58 communicating with the thrombolytic channel and used for injecting thrombolytic drugs, the distal end of the first catheter 51 and/or the stirrer 53 is formed with a plurality of thrombolytic holes 59 for the thrombolytic drugs to enter the blood vessel, wherein, FIG. 19 shows a structure in which thrombolytic holes 59 are located on the first catheter 51, a plurality of thrombolytic holes 59 are evenly distributed along the axial direction of the first catheter 51, and the plurality of thrombolytic holes 59 are located between the proximal and distal ends of the stirrer 53.

Figure 37:
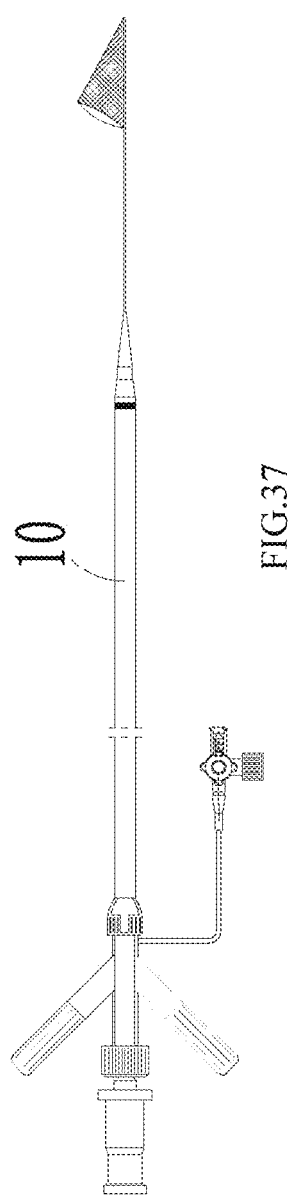
FIG. 37 is a state diagram of the aspiration catheter (excluding the ultrasonic generator) when it cooperates with the filter assembly.
Figure 38:
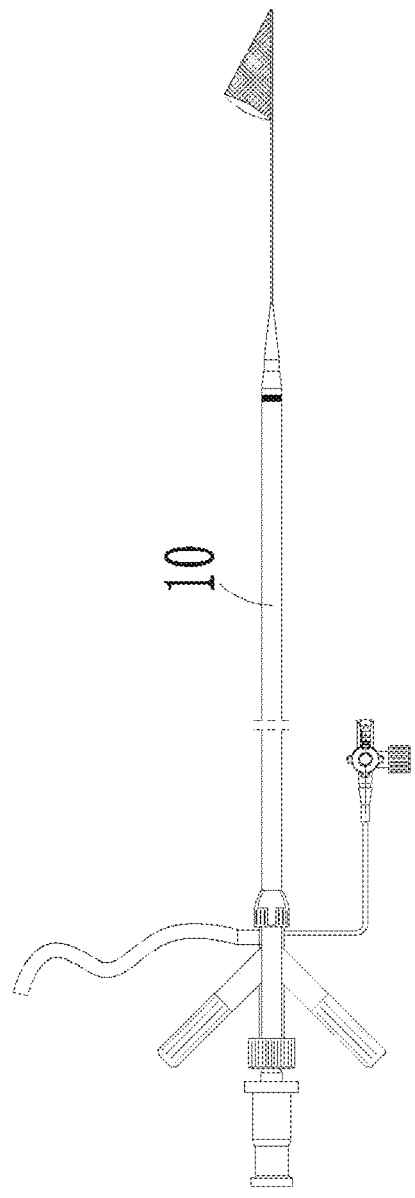
FIG. 38 is a state diagram of the aspiration catheter (including the ultrasonic generator) when it cooperates with the filter assembly.
Figure 39:
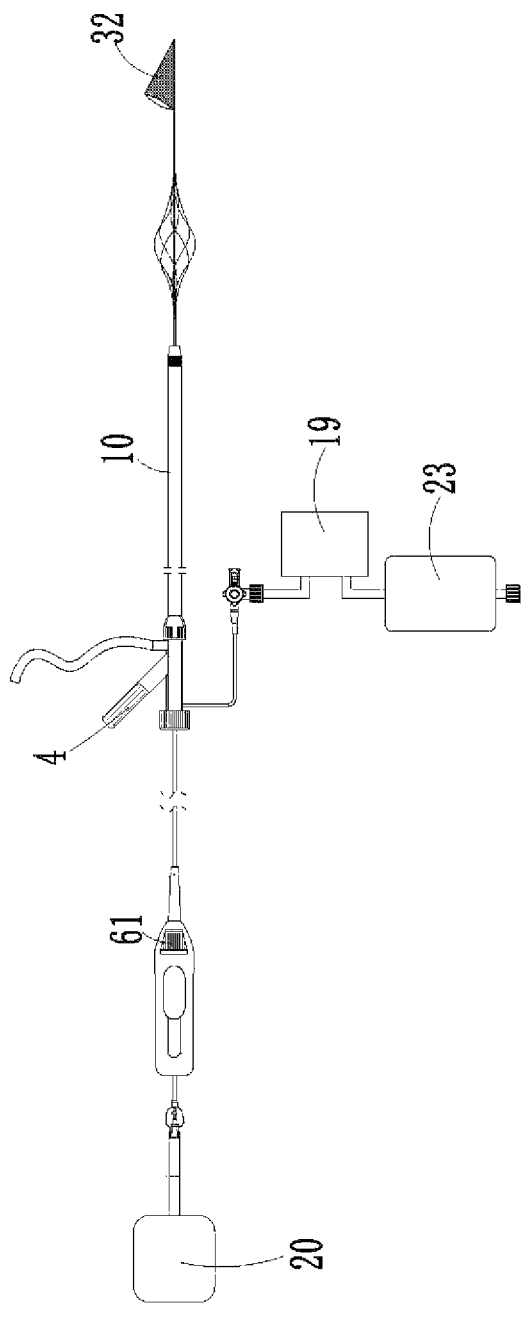
FIG. 39 is a state diagram of the aspiration catheter (including the ultrasonic generator) and the stirring device (excluding the ultrasonic generator) when they cooperate with the filter assembly.
Figure 40:
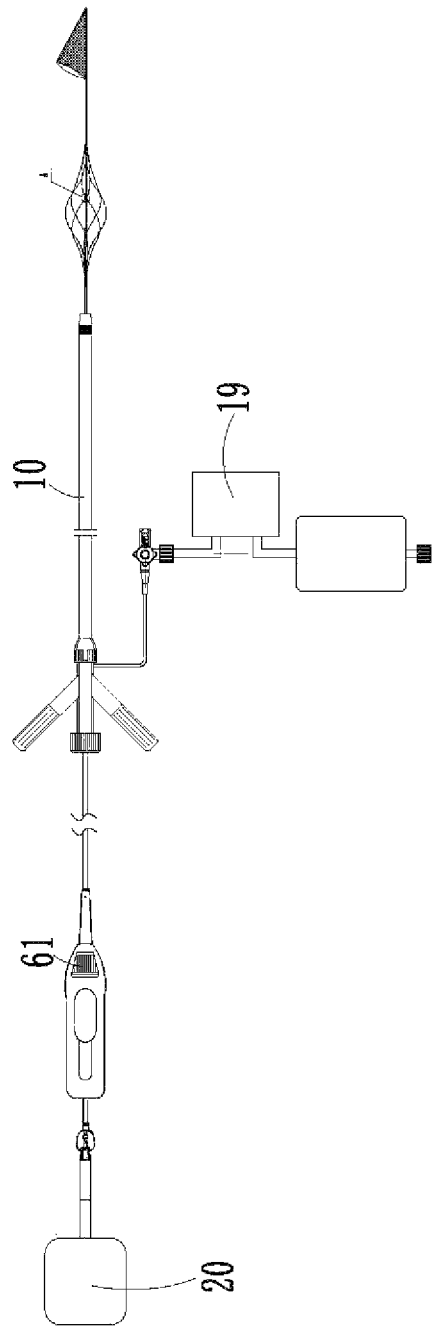
FIG. 40 is a state diagram of the aspiration catheter (excluding the ultrasonic generator) and the stirring device (excluding the ultrasonic generator) when they cooperate with the filter assembly.
Figure 44:
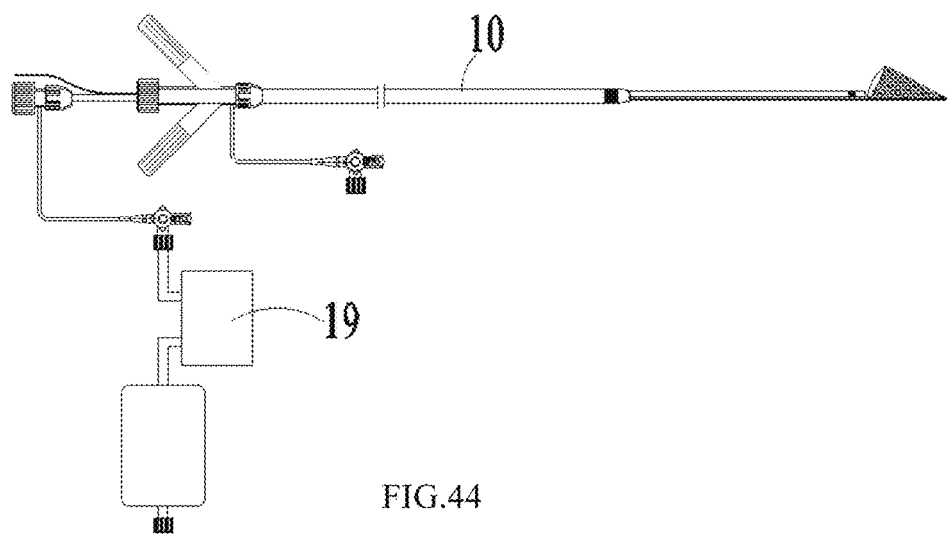
FIG. 44 is a state diagram of the aspiration catheter (excluding the ultrasonic generator) and the sheathing canal when they cooperate with the filter assembly.
Figure 45:
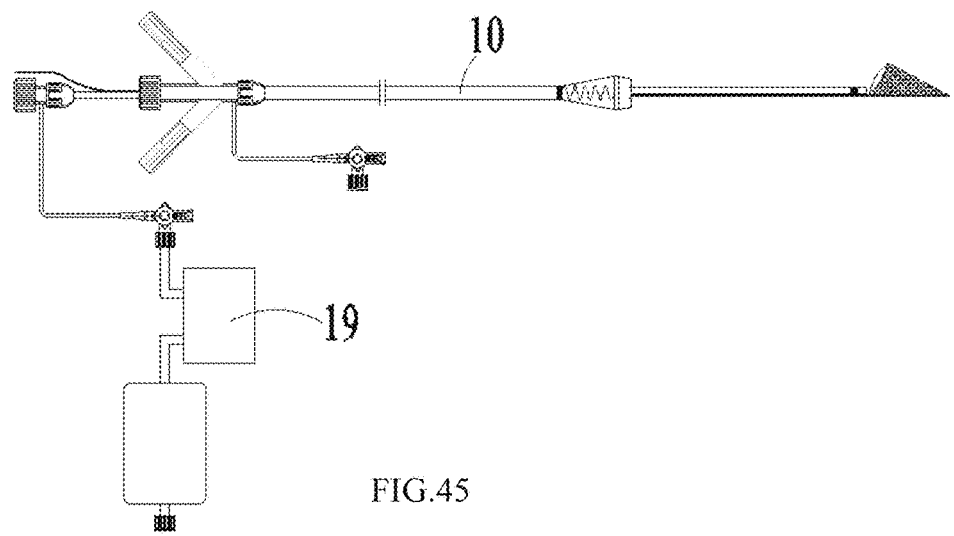
FIG. 45 is a state diagram of the aspiration catheter (including the dilating catheter) and the sheathing canal when they cooperate with the filter assembly.
Figure 46:
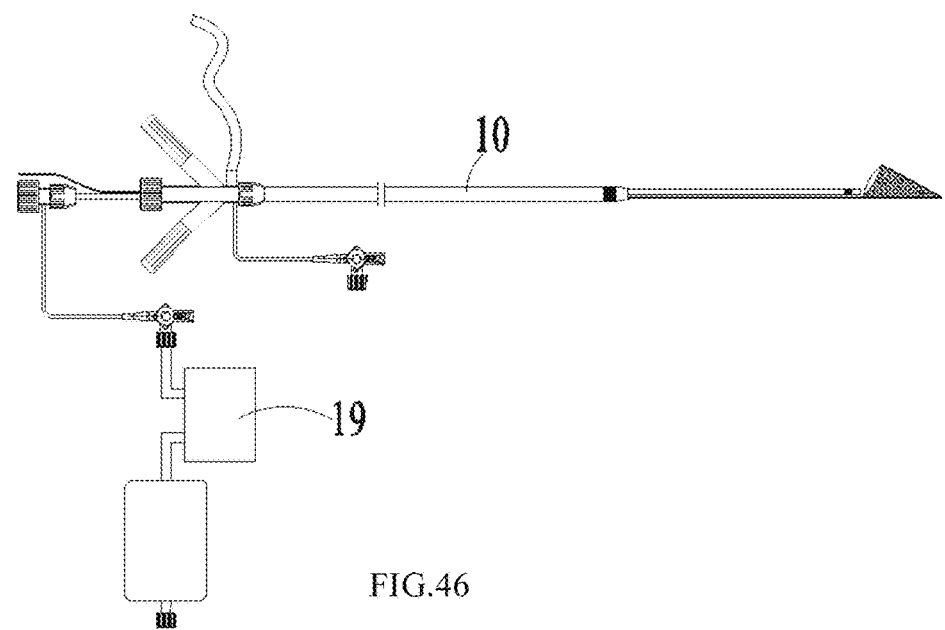
FIG. 46 is a state diagram of the aspiration catheter (including the ultrasonic generator) and the sheathing canal when they cooperate with the filter assembly.

The steps of using this thrombus treatment platform for operation are as follows:

1. First, feeding a 0.035-in guide wire into a designated position;

2. After pushing the 6F sheathing canal 18 loaded with the filter assembly through the 0.035-in guide wire to the site that passes through the thrombus, withdrawing the 6F sheathing canal 18 to expand the filter screen 32, as shown in FIG. 35, withdrawing the 6F sheathing canal 18;

3. Inserting the dilator 9 (its structure shown in FIG. 32) into the aspiration catheter 10, and then pushing it to the designated position of the human body along the filter rod 31, as shown in FIG. 37 or FIG. 38, withdrawing the dilator;

4. Inserting the stirring device into the aspiration catheter 10 along the filter rod 31 and pushing it to the thrombus position, at this time, the stirrer 53 is located between the distal end of the aspiration catheter 10 and the filter screen 32, and in the following, the thrombolysis can be carried out to actual needs or the stirrer 53 can be dragged back and forth or rotated. For example, first injecting the thrombolytic drug from the injection holes 58 into the thrombolytic channel of the first catheter 51, and then into the thrombus through the thrombolytic holes 59 to dissolve the thrombus, after the thrombolysis is completed, sliding the operating member 55 proximally to drive the first catheter 51 slide proximally to expand the stirrer 53, dragging the handle 54 back and forth repeatedly to break and collect the insoluble thrombus, then pressing the operating member 55 to unlock the operating assembly and lock the locking assembly, and activating the motor 20 to drive the first catheter 51, the second catheter 52 and the stirrer 53 to rotate together; or switching on the first ultrasonic generators 81 to generate ultrasonic waves to vibrate the thrombus; at the same time, mounting the aspiration pump 19 on the three-way valve 8 at the proximal end of the aspiration catheter 10, applying negative pressure to the aspiration catheter 10 for aspiration, a recovery bag 23 is connected to the aspiration pump 19 for collecting thrombus, which can prevent large thrombus from drifting during the drag process, as shown in FIGS. 39 to 43;

5. After the operation is over, after withdrawing the stirring device from the body, pushing: the 0.035-in guide wire again to the front end of the filter assembly through the aspiration catheter 10, and inserting the 6F sheathing canal 18 into the aspiration catheter 10 along the 0.035-in guide wire, and pushing it to the front end of the filter assembly, connecting the aspiration pump 19 to the three-way valve 8 of the 6F sheathing canal 18, applying negative pressure to the 6F sheathing canal 18 to aspiration the broken small thrombus intercepted in the filter screen 32, a recovery bag 23 is connected to the aspiration pump 19 for collecting thrombus, and the aspiration negative pressure should preferably not exceed 0.02 MPa to minimize the impact on the deformability of red blood cells and reduce the occurrence of hemolysis as shown in FIG. 45 or 46;

6. After the aspiration is completed, withdrawing the 6F sheathing canal 18 and the 0.035-in guide wire from the body together, and then connecting the aspiration pump 19 to the aspiration catheter 10 to perform aspiration again to remove the remaining thrombus, and then pushing the aspiration catheter 10 distally along the filter rod 31 until the filter screen 32 is completely withdrawn into the aspiration catheter 10, locking the hemostatic valve 7, and withdrawing the entire system to complete the operation.

The present disclosure does not block the blood flow in the blood vessel during the operation, and can prevent the thrombus from drifting downstream in the blood flow during the drag, thrombolysis and aspiration processes. The combined use of the present disclosure in the vein can effectively remove a large area of acute and subacute thrombosis in the inferior vena cava. When dealing with old thrombus of inferior vena cava, thrombolysis can be performed first, and then it is dragged by the stirrer 53, and combined with aspiration and filter protection, the use of this device may remove a large number of thrombus in the inferior vena cava under the condition of ensuring relative safety, protects venous valves and venous vessel walls, has controllable blood loss and simple operation steps, shortens operation time, and reduces patient hospitalization expenses.

As above described, the present disclosure is explained according to the purpose thereof, but the present disclosure is not limited to the above-mentioned embodiments and implementation methods. Various variations and implementations can be made by the practitioners of the relative technical fields within the technical concept of the present disclosure.

What is claimed is:

1. A thrombus treatment platform, comprising an aspiration catheter with an aspiration channel, wherein the thrombus treatment platform further comprises an aspiration pump that communicate with the proximal end of the aspiration catheter, a stirring device, and a filter assembly, the filter assembly comprises a filter rod, and a filter screen fixedly mounted at the distal end of the filter rod and having an expanded state and a collapsed state;

the stirring device comprises a first catheter, a second catheter sliding sleeved outside the first catheter, a stirrer arranged at the distal end of the first catheter and having an expanded state and a collapsed state, and an operating device arranged between the first catheter and the second catheter and capable of causing the first catheter and the second catheter to slide relatively so that the stirrer can be switched between the expanded state and the collapsed state;

the operating device comprises a handle sleeved on the first catheter and/or the second catheter, a locking assembly provided between the first catheter and the second catheter and capable of locking the two relative to each other, and an operating assembly that is slidably connected to the handle and capable of being locked in cooperation with the first catheter or the second catheter;

the aspiration catheter comprises a catheter part with a catheter channel, an operating portion movably connected to the proximal end of the catheter part, a fixing piece fixedly arranged on the catheter part, and a connecting piece respectively connected with the operating portion and the fixing piece and being able to bend the distal end of the catheter part by operating the operating portion;

the thrombus treatment platform further comprises a driving device connected with the first catheter or the second catheter and capable of driving the rotation of the stirrer.

2. The thrombus treatment platform according to claim 1, wherein: when the stirrer is in the collapsed state, the outer diameter of the stirrer is ≤6 F; and/or the degree of expansion of the stirrer is capable being controlled by the second catheter.

3. The thrombus treatment platform according to claim 2, wherein: the stirrer is woven by a plurality of wires, and two ends of each wire are respectively fixed at the proximal end and the distal end of the first catheter; and/or the distal end of the first catheter extends out of the second catheter; the stirrer comprises a plurality of wires; the distal end of each wire is fixedly connected to the first catheter, and the proximal end thereof is fixedly connected to the second catheter.

4. The thrombus treatment platform according to claim 3, wherein: at least part of the wires intersects; at least part of the wires is rotated around the first catheter at a certain angle; the material of the wires is one or more of nickel-titanium alloy, stainless steel wire, and high molecular polymer; and/or the stirring device further comprises a plurality of first ultrasonic generators fixedly arranged on the wires, a first power line connected to the first ultrasonic generators, and a first ultrasonic connector that is provided on the operating device and can power the first power line.

5. The thrombus treatment platform according to claim 4, wherein: the wires have internal cavities, the first catheter or the second catheter also has an internal cavity, and the first power line is located within the internal cavities of the wires and the internal cavity of the first catheter or the second catheter; and/or the diameter of the first ultrasonic generators is 0.2 to 0.4 mm, the outer diameter of the wires is 0.2 to 0.3 mm, and the inner diameter of the wires is 0.1 to 0.2 mm.

6. The thrombus treatment platform according to claim 1, wherein the the locking assembly is in the unlocked state and the operating assembly is in the locked state, when the operating assembly slides relative to the handle, the first catheter and the second catheter slide relatively to cause the stirrer to switch between the expanded state and the collapsed state; when the locking assembly is in the locked state, the relative position of the first catheter and the second catheter is locked, and the driving device is able to drive the first catheter and the second catheter to rotate.

7. The thrombus treatment platform according to claim 6, wherein the locking assembly comprises a first locking member that is fixedly connected to one of the first catheter and the second catheter, a second locking member rotatably connected to the other one of the first catheter and the second catheter, and a third locking member arranged between the first locking member and the second locking member and capable of cooperating with the other one of the first catheter and the second catheter, when the locking assembly is in the locked state, the third locking member is cooperatively locked with the other one of the first catheter and the second catheter, the first locking member and the second locking member.

8. The thrombus treatment platform according to claim 7, wherein: the material of the third locking member is a material that can be elastically deformed, and when the locking assembly is in the locked state, the third locking member is elastically deformed to be tightly mated with the other one of the first catheter and the second catheter, the first locking member and the second locking member, respectively; and/or a groove is formed on the second locking member, an internal thread is formed on the wall of the groove, and an external thread capable of cooperating with the internal thread is formed on an outer surface of the first locking member, the first locking member is inserted in the groove of the second locking member and is rotatably connected with the second locking member through the internal thread and the external thread, and the third locking member is located in the cavity formed by the first locking member and the second locking member.

9. The thrombus treatment platform according to claim 6, wherein the operating assembly comprises an operating member slidably connected to the handle, a mating portion formed on the operating member and capable of being locked in cooperation with the first catheter or the second catheter, and an elastic member that makes the mating portion have a tendency to move toward the state of mating and locking with the first catheter or the second catheter; when the operating assembly is in the locked state, the mating portion and the first catheter or the second catheter are mated and locked; when the operating assembly is in an unlocked state, the mating portion is separated from the first catheter or the second catheter.

10. The thrombus treatment platform according to claim 9, wherein: the operating assembly further comprises a sliding rail fixedly arranged on the inner wall of the handle, a sliding block connected to one end of the elastic member and capable of sliding in cooperation with the sliding rail, and the other end of the elastic member is connected with the mating portion; and/or the stirring device further comprises a plurality of first ultrasonic generators fixedly arranged on the wires, a first power line connected to the first ultrasonic generators, and a first ultrasonic connector that is provided on the operating device and can power the first power line; the wires have internal cavities, the second catheter also has an internal cavity, and the first power line is located within the internal cavities of the wires and the internal cavity of the second catheter; the stirring device further comprises a conductive ring fixed arranged at the proximal end of the first power line; the first catheter comprises a flexible tube section, a metal tube with the distal end fixedly connected to the proximal end of the flexible tube section, an insulating layer sleeved on the part of the metal tube; the material of the mating portion is conductive material, the first ultrasonic connector is connected to the mating portion, and within the effective stroke of the relative movement of the first catheter and the second catheter, the conductive ring is in contact with the metal tube of the first catheter, and the mating portion can contact the metal tube of the first catheter; when the mating portion is in contact with the metal tube of the first catheter, the first ultrasonic connector can supply power to the first ultrasonic generators.

11. The thrombus treatment platform according to claim 1, wherein: the driving device comprises a motor connected to the first catheter or the second catheter, and a power source capable of powering the motor; and/or the first catheter is sheathed on the filter rod, and the outer diameter of the filter rod is 0.1-1 mm; and/or the proximal end of the first catheter is provided with an injection hole for injecting thrombolytic drugs, and the distal end of the first catheter and/or the stirrer is formed with a plurality of thrombolytic holes for the thrombolytic drugs to enter the blood vessel.

12. The thrombus treatment platform according to claim 1, wherein: the operating portion is rotatably connected with the catheter part, the connecting piece has a proximal end and a distal end, the proximal end of the connecting piece is wound around the operating portion, the distal end of the connecting piece is arranged at the distal end of the catheter part; or, the connecting piece has two distal portions located at the distal end and a portion located at the proximal end, and the two distal end portions are respectively arranged on opposite sides of the catheter part, and the proximal end is wound around the operating portion; and/or the operating portion includes a first operating portion movably connected to the proximal end of the catheter part, and a second operating portion movably connected to the proximal end of the catheter part, and the connecting piece includes a first connecting piece and a second connecting piece; the first connecting piece and the second connecting piece have two distal ends located at the distal end and a portion located at the proximal end, respectively, two distal ends of the first connecting piece are respectively arranged on opposite sides of the catheter part, the proximal end of the first connecting piece is arranged around the first operating portion; two distal ends of the second connecting piece are respectively arranged on opposite sides of the catheter part, the proximal end of the second connecting piece is arranged around the second operating portion; and the two distal ends of the first connecting piece and the two distal ends of the second connecting piece are evenly distributed along the circumference of the catheter part; when the first operating portion and the second operating portion are operated, the front end of the catheter part can be oriented and rotated in three-dimensional space.

13. The thrombus treatment platform according to claim 1, wherein the aspiration catheter further comprises a dilating catheter connected to the distal end of the catheter part and having an expanded state and a collapsed state, and when the dilating catheter is in the collapsed state, the dilating catheter is located within the catheter part; when the dilating catheter is in the expanded state, the diameter of the distal end of the dilating catheter is larger than the diameter of the catheter part.

14. The thrombus treatment platform according to claim 13, wherein the dilating catheter comprises a soft membrane fixedly connected to the distal end of the catheter part at its proximal end, and a dilating ring fixedly connected to the distal end of the soft membrane.

15. The thrombus treatment platform according to claim 14, wherein the dilating ring is a memory material or a balloon.

16. The thrombus treatment platform according to claim 1, wherein: the thrombus treatment platform further comprises a second ultrasonic generator arranged at the distal end of the aspiration catheter, a second power line and a second signal transmission line connected with the second ultrasonic generator and arranged in the wall of the aspiration catheter, a second ultrasonic connector arranged at the proximal end of the aspiration catheter and connected to the second power line and the second signal transmission line; and/or the filter screen is in the shape of a basket or a pocket with an opening toward the proximal end, or in the shape of a shuttle.

17. The thrombus treatment platform according to claim 1, wherein the thrombus treatment platform further comprises a sheathing canal that can pass through the aspiration channel and whose distal end extends to the proximal end of the filter screen, and the proximal end of the sheathing canal is connected with an aspiration pump.

18. The thrombus treatment platform according to claim 17, wherein the sheathing canal comprises a first channel for the passage of a guide wire, and a second channel that can allow thrombus to pass through or can receive the filter screen.

19. A thrombus treatment platform, comprising an aspiration catheter with an aspiration channel, wherein the thrombus treatment platform further comprises an aspiration pump that communicate with the proximal end of the aspiration catheter, a stirring device, and a filter assembly, the filter assembly comprises a filter rod passing through the aspiration channel, and a filter screen fixedly mounted at the distal end of the filter rod and having an expanded state and a collapsed state; the filter screen is located at the distal end of the aspiration catheter;

the stirring device comprises a first catheter passing through the aspiration channel, a second catheter passing through the aspiration channel and sliding sleeved outside the first catheter, a stirrer arranged at the distal end of the first catheter and having an expanded state and a collapsed state, and an operating device arranged between the first catheter and the second catheter and capable of causing the first catheter and the second catheter to slide relatively so that the stirrer can be switched between the expanded state and the collapsed state; when the stirrer is in the expanded state, the stirrer is located between the filter screen and the distal end of the aspiration catheter, and when the first catheter is dragged, the stirrer is moved back and forth in the blood vessel;

the operating device comprises a handle sleeved on the first catheter and/or the second catheter, a locking assembly provided between the first catheter and the second catheter and capable of locking the two relative to each other, and an operating assembly that is slidably connected to the handle and capable of being locked in cooperation with the first catheter or the second catheter;

the aspiration catheter comprises a catheter part with a catheter channel, an operating portion movably connected to the proximal end of the catheter part, a fixing piece fixedly arranged on the catheter part, and a connecting piece respectively connected with the operating portion and the fixing piece and being able to bend the distal end of the catheter part by operating the operating portion;

the thrombus treatment platform further comprises a driving device connected with the first catheter or the second catheter and capable of driving the rotation of the stirrer.

\* \* \* \* \*